US009492220B2

(12) United States Patent
McGreevy et al.

(10) Patent No.: US 9,492,220 B2
(45) Date of Patent: *Nov. 15, 2016

(54) APPARATUS AND METHOD FOR RAPID RELIABLE ELECTROTHERMAL TISSUE FUSION

(75) Inventors: Francis T. McGreevy, Aurora, CO (US); Katherine R. Pavlovsky, Denver, CO (US)

(73) Assignee: Conmed Corporation, Utica, NY (US)

( * ) Notice: Subject to any disclaimer, the term of this patent is extended or adjusted under 35 U.S.C. 154(b) by 2147 days.

This patent is subject to a terminal disclaimer.

(21) Appl. No.: 11/701,857

(22) Filed: Feb. 1, 2007

(65) Prior Publication Data
US 2008/0187989 A1   Aug. 7, 2008

(51) Int. Cl.
*A61B 18/14*   (2006.01)
*A61B 18/08*   (2006.01)
(Continued)

(52) U.S. Cl.
CPC ............... *A61B 18/14* (2013.01); *A61B 18/08* (2013.01); *A61B 18/085* (2013.01); *A61B 18/1206* (2013.01); *A61B 18/1442* (2013.01);
(Continued)

(58) Field of Classification Search
CPC  A61B 18/08; A61B 18/085; A61B 18/1206; A61B 18/14; A61B 18/1442; A61B 2018/00089; A61B 2018/00095; A61B 2018/00589; A61B 2018/0063; A61B 2018/00636; A61B 2018/00642; A61B 2018/00648; A61B 2018/00654; A61B 2018/00702; A61B 2018/00791; A61B 2018/00797; A61B 2018/145; A61B 2562/0261

USPC .......................... 606/45, 48, 51–52
See application file for complete search history.

(56) References Cited

U.S. PATENT DOCUMENTS

| 5,021,634 A | 6/1991 | Santoro et al. |
| 5,196,009 A | 3/1993 | Kirwan, Jr. |
| 5,423,814 A | 6/1995 | Zhu et al. |

(Continued)

FOREIGN PATENT DOCUMENTS

| WO | WO 96/20652 | 7/1996 |
| WO | WO 97/11649 | 4/1997 |

(Continued)

OTHER PUBLICATIONS

PCT International Search Report with attached Written Opinion of the International Searching Authority for International Application No. PCT/US2008/001168, dated Jul. 10, 2008, 11 pages.

(Continued)

*Primary Examiner* — Michael Peffley
*Assistant Examiner* — Samantha Good
(74) *Attorney, Agent, or Firm* — Frederick J. M. Price; Bond, Schoeneck & King, PLLC

(57) ABSTRACT

Pieces of tissue are fused together by compressing the pieces together at an interface, delivering an impulse of electrical power which is converted into sufficient thermal energy to fuse the pieces together at the interface. The impulse and the fusion occur within a preferable time of 0.5-2.0 seconds but no greater than 4.0 seconds. The temperature of the thermal energy is regulated between 150° C.-200° C. The tissue pieces are compressed to a thickness of 0.05-0.10 mm. Jaws which compress the tissue and transfer the energy have smooth working surfaces with an Ra of 0.15 or less microns to 0.40 microns.

32 Claims, 14 Drawing Sheets

(51) Int. Cl.
*A61B 18/12* (2006.01)
*A61B 18/00* (2006.01)

(52) U.S. Cl.
CPC .............. *A61B2018/0063* (2013.01); *A61B 2018/00702* (2013.01); *A61B 2018/00791* (2013.01)

(56) References Cited

U.S. PATENT DOCUMENTS

| | | | |
|---|---|---|---|
| 5,596,813 | A | 1/1997 | Olson, Jr. et al. |
| 5,707,369 | A | 1/1998 | Vaitekunas |
| 5,749,893 | A | 5/1998 | Vidal et al. |
| 5,827,271 | A | 10/1998 | Buysse et al. |
| 5,891,142 | A | 4/1999 | Eggers et al. |
| 6,162,217 | A | 12/2000 | Kannenberg et al. |
| 6,174,309 | B1 | 1/2001 | Wrublewski et al. |
| 6,235,027 | B1 | 5/2001 | Herzon |
| 6,293,946 | B1 | 9/2001 | Thorne |
| 6,298,550 | B1 | 10/2001 | Kirwan, Jr. |
| 6,312,428 | B1* | 11/2001 | Eggers et al. ............ 606/41 |
| 6,582,451 | B1 | 6/2003 | Marucci et al. |
| 6,626,901 | B1 | 9/2003 | Treat et al. |
| 6,740,085 | B2 | 5/2004 | Hareyama et al. |
| 6,923,806 | B2* | 8/2005 | Hooven et al. ............ 606/41 |
| 6,939,346 | B2 | 9/2005 | Kannenberg et al. |
| 6,939,347 | B2 | 9/2005 | Thompson |
| 6,966,909 | B2 | 11/2005 | Marshall et al. |
| 7,011,656 | B2 | 3/2006 | McGaffigan et al. |
| 7,131,445 | B2 | 11/2006 | Amoah |
| 7,196,295 | B2 | 3/2007 | Fennewald et al. |
| 2002/0091383 | A1 | 7/2002 | Hooven |
| 2003/0060818 | A1* | 3/2003 | Kannenberg et al. ......... 606/34 |
| 2003/0073987 | A1* | 4/2003 | Sakurai et al. .............. 606/28 |
| 2003/0125735 | A1* | 7/2003 | Herzon ...................... 606/51 |
| 2003/0139741 | A1 | 7/2003 | Goble et al. |
| 2003/0187429 | A1 | 10/2003 | Karasawa et al. |
| 2003/0199870 | A1 | 10/2003 | Truckai et al. |
| 2003/0216733 | A1 | 11/2003 | McClurken et al. |
| 2004/0015163 | A1 | 1/2004 | Buysse et al. |
| 2004/0092923 | A1 | 5/2004 | Miura et al. |
| 2005/0021017 | A1 | 1/2005 | Karasawa et al. |
| 2005/0103352 | A1* | 5/2005 | McGaffigan et al. ......... 128/898 |
| 2005/0113828 | A1 | 5/2005 | Shields et al. |
| 2005/0165429 | A1 | 7/2005 | Douglas et al. |
| 2005/0165444 | A1 | 7/2005 | Hart et al. |
| 2005/0240179 | A1* | 10/2005 | Buysse et al. ............ 606/51 |
| 2008/0187989 | A1 | 8/2008 | McGreevy et al. |
| 2008/0188844 | A1 | 8/2008 | McGreevy et al. |

FOREIGN PATENT DOCUMENTS

| | | |
|---|---|---|
| WO | WO 97/42892 | 11/1997 |
| WO | WO 99/40858 | 8/1999 |
| WO | WO 01/64122 | 9/2001 |

OTHER PUBLICATIONS

PCT International Search Report with attached Written Opinion of the International Searching Authority for International Application No. PCT/US2008/001180, dated Jul. 10, 2008, 12 pages.
PCT International Search Report with attached Written Opinion of the International Searching Authority for International Application No. PCT/US2008/001171, dated Jun. 11, 2008, 11 pages.
Watlow Ultramic 600 Advanced Ceramic Heater, brochure, Nov. 2006, 6 pages.
J. W. Fenner et al., Dehydration: a model for (low-temperature) argon laser tissue bonding, Phys. Med. Biol. 39 (1994), printed in the UK, pp. 2147-2160.
P. Mertyna et al., Radiofrequency ablation: The effect of distance and baseline temperature on thermal dose required for coagulation, Int. F. Hyperthermia, Nov. 2008; 24(7), pp. 550-559.
Chang-Hwan Choi et al., Cell Adhesions on Nanoturf Surfaces, UCLA Mechanical & Aerospace Engineering Dept. and Bioengineering Dept., Jan. 2006, pp. 402-405.
Paul Roach et al., Progess in superhydrophobic surface development, journal, Soft Matter, 2008, The Royal Society of Chemistry 2008, Oct. 30, 2007, pp. 224-240.
Jenifer Kennedy et al., Controlled Radio Frequency Vessel Sealing System for Surgical Applications, SPIE vol. 3249, Jan. 25, 1998, pp. 125-129.

* cited by examiner

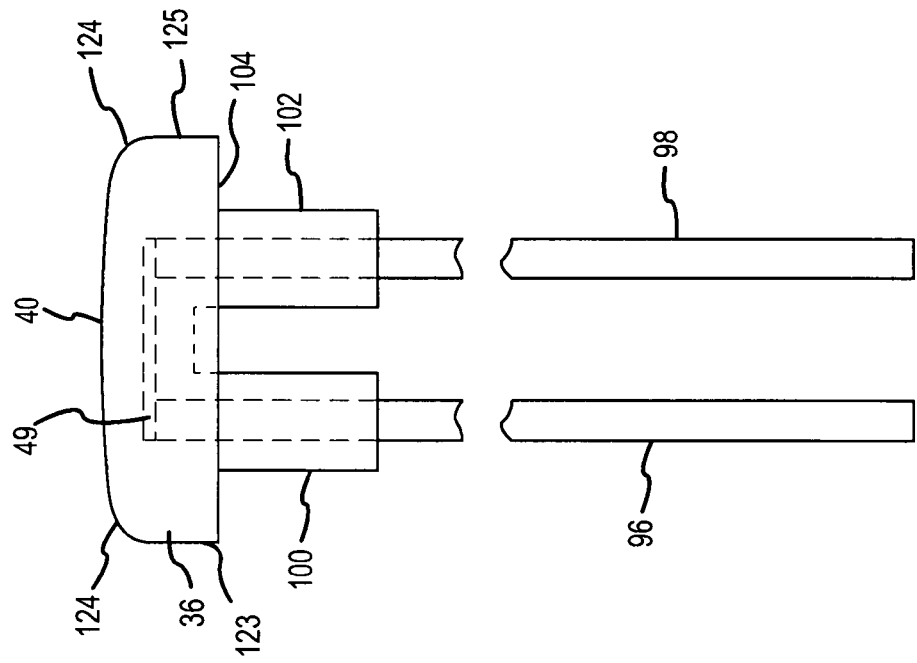
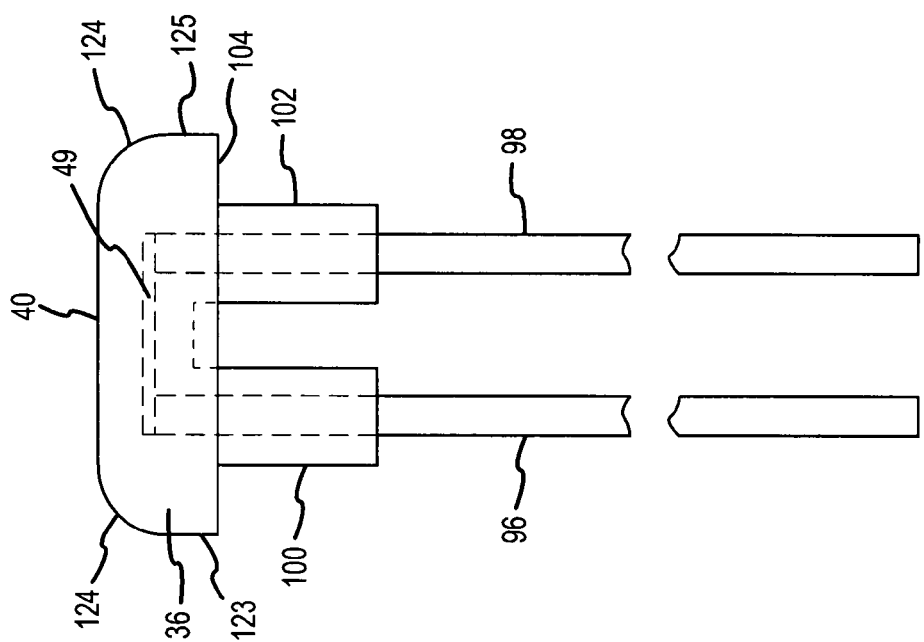

APPARATUS AND METHOD FOR RAPID RELIABLE ELECTROTHERMAL TISSUE FUSION

CROSS REFERENCE TO RELATED APPLICATIONS

This invention is related to inventions for an Apparatus and Method for Rapid and Reliable Electrothermal Tissue Fusion and Simultaneous Cutting, described in U.S. patent application Ser. No. 11/701,884, and for an Tissue Fusion Instrument and Method to Reduce the Adhesion of Tissue to its Working Surfaces, described in U.S. patent application Ser. No. 11/701,858, both filed concurrently herewith by the inventors hereof and assigned to the assignee of the present invention. The disclosures of these concurrently-filed U.S. patent application are incorporated herein by this reference.

FIELD OF THE INVENTION

This invention relates to electrothermal tissue fusion, and more particularly, to a new and improved electrothermal apparatus and electrothermal method that seals or fuses tissue with the application of a short time-duration impulse of electrical energy which creates relatively high temperature heat that is applied to squeezed-together tissue pieces. The seal is achieved quickly and is of high integrity to resist failure. However, in the unlikely event of failure, the seal exhibits a beneficial failure mode which is effective in avoiding internal bleeding.

BACKGROUND OF THE INVENTION

Coaptive electrothermal tissue fusion or sealing involves the application of force and electrical energy to heat compressed tissue sufficiently to join together separate pieces of tissue. Electrothermal tissue fusion avoids the need to manually suture or tie-off tissues or vessels during a surgical procedure.

Although the exact details of the physical chemistry involved in tissue fusion are probably not completely understood, it is believed that the heat denatures chains or strands of tissue proteins in the separate pieces of tissue and the pressure causes the denatured protein chains to reconstitute or re-nature across the interface between the tissue pieces. The reconstituted proteins chains interact and intertwine with one another to hold the previously-separate tissues pieces together.

Collagen is one type of protein chain that appears to play an important role in tissue fusion. Collagen, also known as tropocollagen, consists of three polypeptide protein chains that form a triple helix. These protein chains are grouped or tangled together to establish significant tissue structure and strength, as is observed in blood vessels and ligaments. Applying heat to the tissue to raise the temperature to about 60-70° C. causes the protein chains to become disordered, disassociated, separated and untangled from the triple helix.

Elastin is another type of protein chain that appears to play an important role in tissue fusion. Elastin a collection of polypeptide protein chains that are individually and randomly cross-linked with each other to form a fibril. Fibrils are grouped or tangled together to form an elastin fiber. Upon the application of heat to raise the temperature to about 120° C., the elastin fiber becomes disassociated into a disordered collection of individual polypeptide chains, fibrils and fibers.

The heat which causes denaturation of the collagen and elastin chains also appears to create unfavorable molecular interactions among the components of the denatured proteins, resulting in a relatively high free energy state. Atoms with the same electrostatic charge, and hydrophobic and hydrophillic regions of the protein chains, begin to interact and create repulsive forces. Force must be applied at the interface between the tissue pieces during fusion to overcome the repulsive forces and to achieve more favorable interactions of the proteins chains thereby reducing the amount of free energy. Force must also be applied at the interface to maintain the denatured protein chains in physical proximity with each other so that they will reconstitute and join the tissue pieces together.

Although this theoretical model of tissue fusion is understandable, reliable tissue fusion is difficult to achieve on a consistent basis. Fusing blood vessels is of particular concern, because vessel fusion during a surgical procedure is the primary use of tissue fusion at the present time. Fused blood vessels that fail or leak after the conclusion of surgery lead to internal bleeding. Internal bleeding usually requires a second operation to gain access to and seal the leaking vessel, which induces further trauma and risk to the patient.

One prior art type of electrosurgical tissue fusion involves bipolar electrosurgery. The tissues are compressed between two jaws of a forceps-type instrument. The jaws also serve as electrodes to conduct high-voltage radio frequency (RF) current through the compressed tissue. Heat is generated from the RF current flowing through the resistance or impedance of the tissue, and that heat denatures the chains of protein.

Certain difficulties arise when using bipolar electrosurgical tissue fusion. The voltage between the jaws which compress the tissue and serve as electrodes is typically several thousand volts. The distance between the jaws is relatively small when the tissue is compressed. The relatively high voltage can create arcs which jump the small distance between the jaws and penetrate the tissue adjacent to the jaws, particularly toward the end of the fusion procedure when the tissue between the jaws dehydrates and its impedance increases. The arcs enter the tissue in minuscule spots and destroy or weaken the tissue at those spots. Under conditions of prolonged application of RF power in this manner, which is typical with bipolar electrosurgical tissue fusion, the arcing can actually perforate the tissue adjacent to the fused area, thereby rupturing the tissue and destroying any sealing effect from the sealed area if there are a significant number of ruptures. This is particularly the case when sealing vessels, because a typical failure mode of vessels sealed with bipolar electrosurgery is a leak or rupture in the wall of the vessel adjacent to the sealed area.

The RF current inherently flows through the tissue in a somewhat random or uncontrollable pattern depending on the point-to-point characteristics of the tissue and many other factors. As a consequence, uniform heating of the tissue is impossible to control. The non-homogeneous distribution of heat over the area to be fused causes the protein chains to denature and reconstitute in a variable and nonuniform manner. The nonuniform denaturation and reconstitution leads to fused tissue areas of variable, nonuniform and somewhat unpredictable strength.

Assessing when to stop the delivery of RF current during bipolar electrosurgical tissue fusion is difficult. Applying either too much or too little RF current leads to seals that are more likely to fail. The application of too much RF current creates an excessive amount of heat which drives chemical reactions that appear to oxidize or burn the tissue and change the nature of the protein chains, thereby diminishing their ability to reconstitute and create effective seals. Overly-heated tissue at the sealed area or adjacent to the sealed area increases the probability of a failure because the tissue has become brittle and lacks pliability due to excessive dehydration, thereby contributing to cracking and breaking. In contrast, prematurely stopping the delivery of RF current prevents an adequate amount of denaturing of the protein chains which, in turn, prevents an adequate amount of reconstitution of the proteins chains, thereby diminishing the strength of the seal.

Control systems have been developed to attempt to address the problem of applying too much or too little RF power during bipolar electrosurgical tissue fusion. Such control systems monitor some event associated with the application of electrical power to the tissue, typically the impedance. Monitoring the tissue impedance is based on an expectation that some change indicates the occurrence of appropriate sealing conditions. However, it is believed that no reliable relationship exists between tissue impedance and the formation of a consistently reliable seal.

Another problem with bipolar electrosurgical tissue fusion is that the alternating aspects of the RF electrical energy inherently results in less energy application per unit of time. The alternating aspects of the RF energy application is by nature a pulsed or alternating current (AC) energy application, as opposed to a continual energy application. The tissue must withstand relatively high voltages, but the amount of power transferred is not commensurate with the high voltage due to the pulsed or AC application of the RF current. The effect of the pulsed or alternating RF energy application is that more time is required to transfer an equivalent amount of energy compared to the transfer of energy delivered at a sustained peak value. The typical maximum power delivery with a widely used RF tissue fusion device is approximately 115 to 350 Watts per square inch (18-56 W/cm$^2$).

Electrothermal instruments have also been used for tissue fusion. Electrothermal instruments have heating elements within jaws that grip and compress the tissue. Electrical current is conducted through the heating elements to generate the heat that is applied to the compressed tissue. As with bipolar electrosurgery, previous electrothermal instruments have produced varying and inconsistent tissue fusion results, possibly as a result of an ineffective control system or control functionality based on misperceptions relating to tissue fusion physiology, including the perceived limitation of not heating the tissue above the 120° C. point where elastin protein chains denature. The prevalent view is to avoid elevating the temperature of the tissue beyond the 120° C. point where elastin protein chains denature, because it is believed that temperatures beyond that point are destructive to the proteins chains. Consequently, all presently known tissue fusion technologies attempt to limit the tissue temperature to no more than approximately 120° C., and many tissue fusion technologies limit the temperature of the tissue to approximately 100° C. to avoid creating steam.

Although the principal concern of tissue fusion is creating reliable seals that hold on a long-term basis, another very important practical consideration is an ability to create seals quickly. A typical surgical procedure will involve sealing many blood vessels at the surgical site. The typical time required by known electrosurgical tissue sealing devices to create a single seal is about 5-12 seconds. A considerable amount of time is therefore consumed in making each seal. Considering that a typical surgical procedure may require sealing scores of vessels, a considerable amount of the total procedure time is consumed by vessel sealing.

Moreover, because of concern about the reliability of the vessel seals, the typical practice is to create two sequential seals at each severed end of the vessel. The theory is that if the first or upstream seal fails, the second or downstream seal becomes a redundant backup to prevent fluid leakage. The time to create the primary and backup seals is more than twice the amount of time required to create a single seal when the time for repositioning and observing the quality of each seal is taken into account. Further still, double seals must be made at both ends of each severed vessel. Thus, a considerable amount of time is consumed during the surgical procedure by sealing vessels. The time consumed by sealing vessels extends the time required to accomplish the entire surgical procedure, or alternatively, detracts from the time available to accomplish other activities during the surgical procedure.

SUMMARY OF THE INVENTION

The present invention creates reliable seals of good integrity, and does so in a considerably shorter amount of time than known tissue sealing techniques. The present invention delivers a short impulse of a relatively high amount of electrical energy to create the heat applied to the forced-together interface of the two tissues. Reliable seals having good structural integrity can be formed with an electrical power impulse having a duration of about 0.5 to 2.0 seconds, but in certain exaggerated circumstances, a time duration of the electrical power impulse may extend to about 4.0 seconds. The amount of energy delivered is sufficient to elevate the jaw temperature at the interface to between 150° C. and 200° C. The relatively short time duration of the energy impulse and the resulting high temperature quickly create an effective, reliable and consistent seal which has improved failure mode characteristics.

The short time duration of the high temperature does not adversely affect the ability of the protein chains to renature and thereafter reconstitute in a strong reliable bond, even though the temperature created is considerably higher than the typically-regarded appropriate temperature for tissue fusion. The short impulse of relatively high heat is believed to effectively dehydrate or desiccate polar water molecules from binding sites on the protein chains without so dehydrating the tissue as to substantially compromise its pliability, thereby permitting more and direct interactions between the protein chains at those binding sites, resulting in stronger direct interactions between the protein chains, increased affinity between the chains and increased strength of the fusion between the tissues at the interface. However, the short impulse of energy does not so dehydrate the sealed and adjacent tissue to cause it to lose its pliability and strength and thereby contribute to a leak or seal failure.

The seal created by the relatively short impulse of high energy becomes effective immediately, allowing the compression force on the tissue to be released almost immediately after delivering impulse of energy, without requiring a cooling-off time period. Both the short amount of time required to create the seal and the avoidance of a subsequent cooling-off period greatly diminish the amount of time required to complete each seal.

The quick delivery of energy forms an effective seal without significantly destroying or substantially adversely affecting the strength of the tissue adjacent to the seal. Consequently, the adjacent tissue retains its natural strength and is unlikely to fail, unlike the typical prior art tissue seal which is created after considerable thermal energy has been spread to the adjoining tissue. The thermal spread to the adjoining tissue is believed to destroy or diminish the strength of the adjacent tissue, making it susceptible to rupture from physiological pressure even though the sealed area itself may remain intact.

The sealed areas have a consistent strength which is significantly greater than the normal physiological pressure applied on the sealed area. The strength and integrity minimizes or virtually eliminates post-operative bleeding. The reliability and integrity of the seals diminishes or eliminates the need for double seals for redundancy purposes. However, under circumstances where double seals are preferred, the characteristics of the seal created assure that a failure of the primary upstream seal will still confine the fluid to the vessel so that the redundant downstream seal will have the opportunity to function as an effective backup.

In accordance with these and other features, one aspect of the invention is an apparatus for fusing together pieces of tissue at an interface. The apparatus comprises a tissue fusion instrument and a power control device. The tissue fusion instrument includes jaws with working surfaces and a movement mechanism which moves the jaws toward one another to compress the tissue pieces together at the interface between the working surfaces. The working surfaces are formed of ceramic material and have a smoothness defined by an Ra of 0.40 microns or less. The movement mechanism compresses the tissue pieces at the interface with sufficient force to achieve a compressed tissue thickness sufficient to fuse the tissue pieces at the interface, which in the case of blood vessels is 0.05 mm to 0.10 mm. The power control device delivers an impulse of electrical power to the jaws which contains sufficient energy to fuse the tissue pieces together at the interface within no greater than 4.0 seconds after the electrical power impulse is initiated. The power impulse creates thermal energy and maintains a temperature of the thermal energy applied to the interface in the range of 150° C. to 200° C.

Another aspect of the invention is an apparatus for fusing together pieces of tissue at an interface, and the apparatus comprises a tissue fusion instrument and a power control device. The tissue fusion instrument includes jaws with working surfaces and a movement mechanism which moves the jaws toward one another to compress the tissue pieces together at the interface between the working surfaces. The power control device delivers an impulse of electrical power to the jaws which contains sufficient energy to fuse the tissue pieces together at the interface with a temperature applied to the interface in the range of 150° C. to 200° C. for no greater than 2.0 seconds after the electrical power impulse is initiated.

A further aspect of the invention is a method of electrothermally fusing together pieces of tissue at an interface. The method involves compressing the tissue pieces together at the interface, delivering an impulse of electrical power which contains sufficient energy to fuse the tissue pieces together at the interface within no greater than 4.0 seconds, converting the electrical power impulse into thermal energy applied at the interface, and regulating the temperature of the thermal energy applied at the interface in a range of 150° C. to 200° C. while fusing the tissue pieces.

Preferably, the time duration of the electrical power impulse is between 0.5 seconds to 2.0 seconds. The invention is particularly applicable to fusing apposite walls of a vessel of up to 8 mm in diameter to form an occlusion in a lumen of the vessel. The invention is also particularly useful for creating double seals in vessels because the strength between the tissue pieces at the interface from the fusion is less than the inherent strength of each tissue piece at the fused interface to allow separation of the tissue pieces at the interface before breaching the tissue pieces at or adjoining the interface. These characteristics advantageously allow the second of the double seals to become effective as a redundant seal should the first or upstream seal fail.

Certain further aspects of the invention involve one or more of the following features: releasing compression of the interface immediately after termination of the electrical power impulse, elevating the temperature of the thermal energy applied at the compressed interface at a rate of between 150° C. per second to 500° C. per second from energy contained in the electrical power impulse, producing an energy density in the range of 233 W per square centimeter to 388 W per square centimeter of area of the compressed interface from the electrical power impulse, forming electrical power impulse from direct current and conducting the direct current power impulse to a heating element within each jaw, releasing compression of the interface after fusion by moving the working surfaces away from the fused interface with the working surfaces extending parallel to one another, releasing compression of the interface without inducing shear forces on the fused interface, and separately regulating characteristics of the electrical power impulse delivered to the heating element within each jaw to regulate the temperature of thermal energy applied by the working surface from each jaw separately.

A more complete appreciation of the present disclosure and its scope, and the manner in which it achieves the above and other improvements, can be obtained by reference to the following detailed description of presently preferred embodiments taken in connection with the accompanying drawings, which are briefly summarized below, and to the appended claims.

BRIEF DESCRIPTION OF THE DRAWINGS

FIG. 11 is an end elevational view of one form of the working surface of the bottom jaw shown in FIG. 8.

FIG. 12 is an end elevational view of another form of the working surface of the bottom jaw shown in FIG. 11, which is an alternative to that shown in FIG. 11.

DETAILED DESCRIPTION

Figure 1:
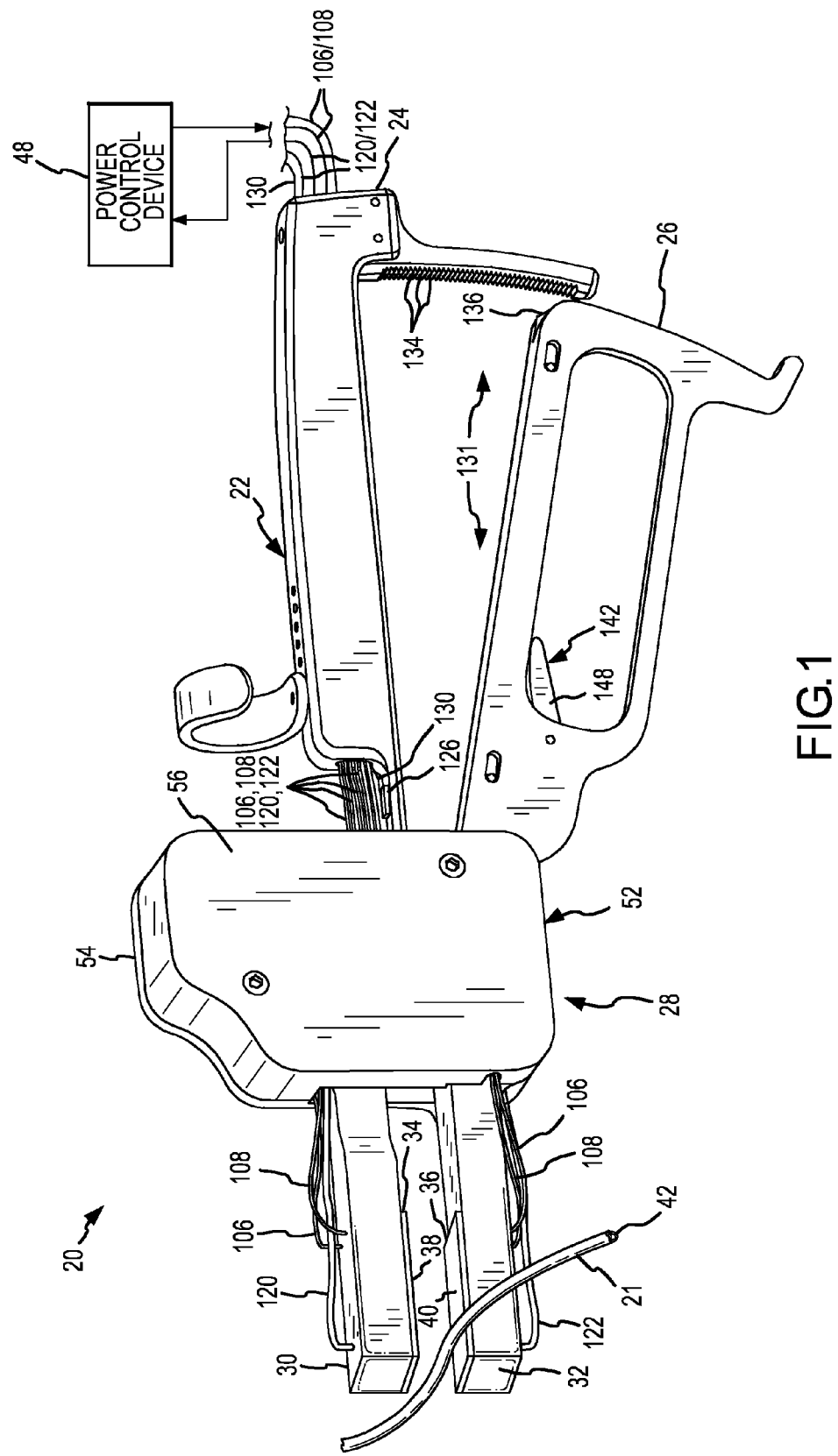
FIG. 1 is an illustration of an electrothermal tissue fusion or sealing apparatus which incorporates the present invention and which comprises a tissue fusion instrument, shown in a perspective view, and a power control device, shown in block diagram form, which are used to seal a vessel, shown in perspective.
Figure 2:
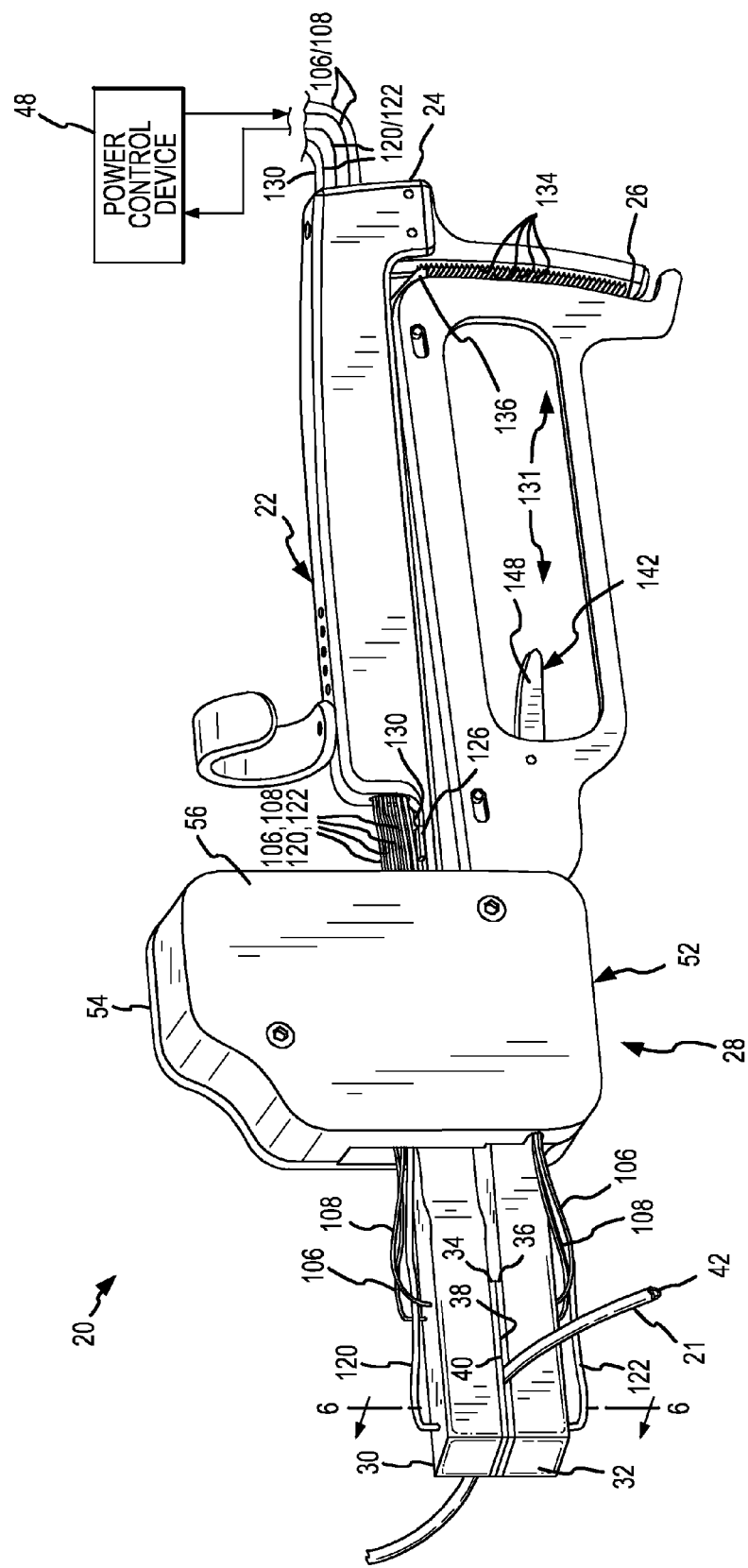
FIG. 2 is an illustration of the use of the tissue fusion apparatus shown in FIG. 1 to fuse a vessel.
Figure 3:
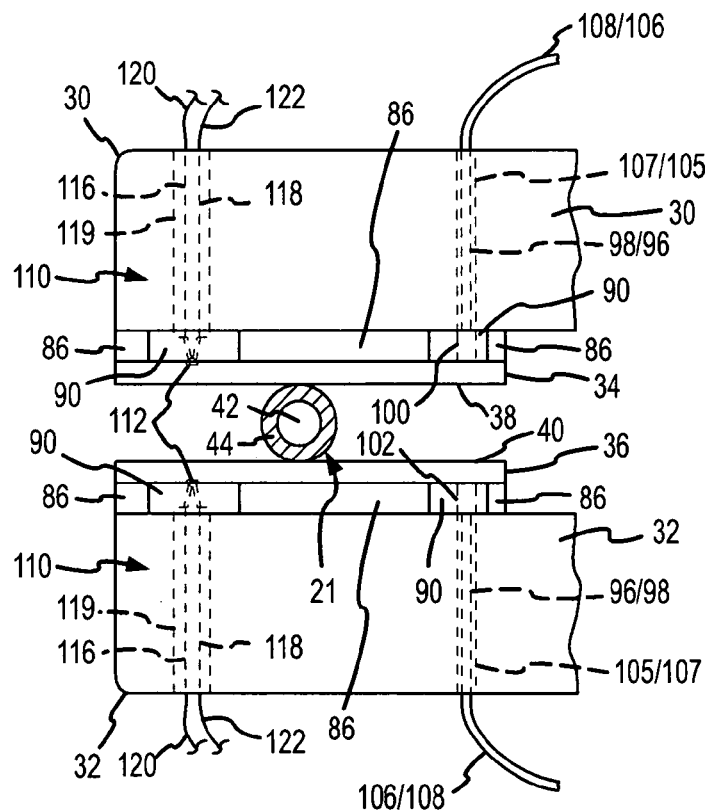
FIG. 3 is an enlarged side elevational view of distal arms and jaws of the tissue fusion instrument and a cross-sectional view of the vessel shown in FIG. 1, before compressing the vessel when fusing it.

The present invention is incorporated in an electrothermal tissue fusion or sealing apparatus 20 shown in FIG. 1. The electrothermal apparatus 20 is used to fuse or seal biological tissue, such as a vessel 21, by use of a handpiece or tissue fusion instrument 22. Proximal handles 24 and 26 of the instrument 22 are moved or squeezed together, which causes a parallel movement mechanism 28 (FIG. 6) of the instrument 22 to move distal arms 30 and 32 of the instrument 22 toward one another with parallel closing movement. Jaws 34 and 36 are attached to the distal end of the arms 30 and 32. Working surfaces 38 and 40 of the jaws 34 and 36 contact, squeeze, force and compress the vessel 21 when the jaws 38 and 40 and the distal arms 30 and 32 move toward one another, as shown in FIG. 2. Before compression, a lumen 42 within the vessel 21 is unobstructed and not occluded as shown in FIG. 3. Movement of the jaws 34 and 36 toward one another forces and compresses walls 44 of the vessel 21 into apposition with one another at a tissue interface 46 shown in FIG. 4.

An impulse of electrical energy from a power control device 48, shown in FIGS. 1 and 2, is delivered to a heating element 49 (FIGS. 7 and 9-12) embedded in each of the jaws 34 and 36, upon compressing together the apposite walls 44 of the vessel 21 at the tissue interface 46. The heating element 49 converts the electrical power to heat, and the heat is conducted from the working surfaces 38 and 40 to elevate the temperature of the compressed apposite vessel walls 44 at the interface 46. The temperature of the vessel walls 44 is elevated to a predetermined set point temperature within the range of 150° C. to 200° C. where tissue fusion occurs while the jaws 34 and 36 hold the apposite vessel walls 44 against one another with a force to achieve a thickness of from 0.05 mm to 0.10 mm of the fully compressed and heated vessel walls. Types of tissues other than blood vessels may require a different amount of pressure or may be fused with a different compressed thickness at the interface. In the embodiment of the electrothermal instrument 20 described herein in which the working surfaces of the jaws 34 and 36 have a width of approximately 5 mm and a length of approximately 25 mm, the amount of force typically transferred to the tissue is from 110 Newtons (N) to 150 N.

Figure 5:
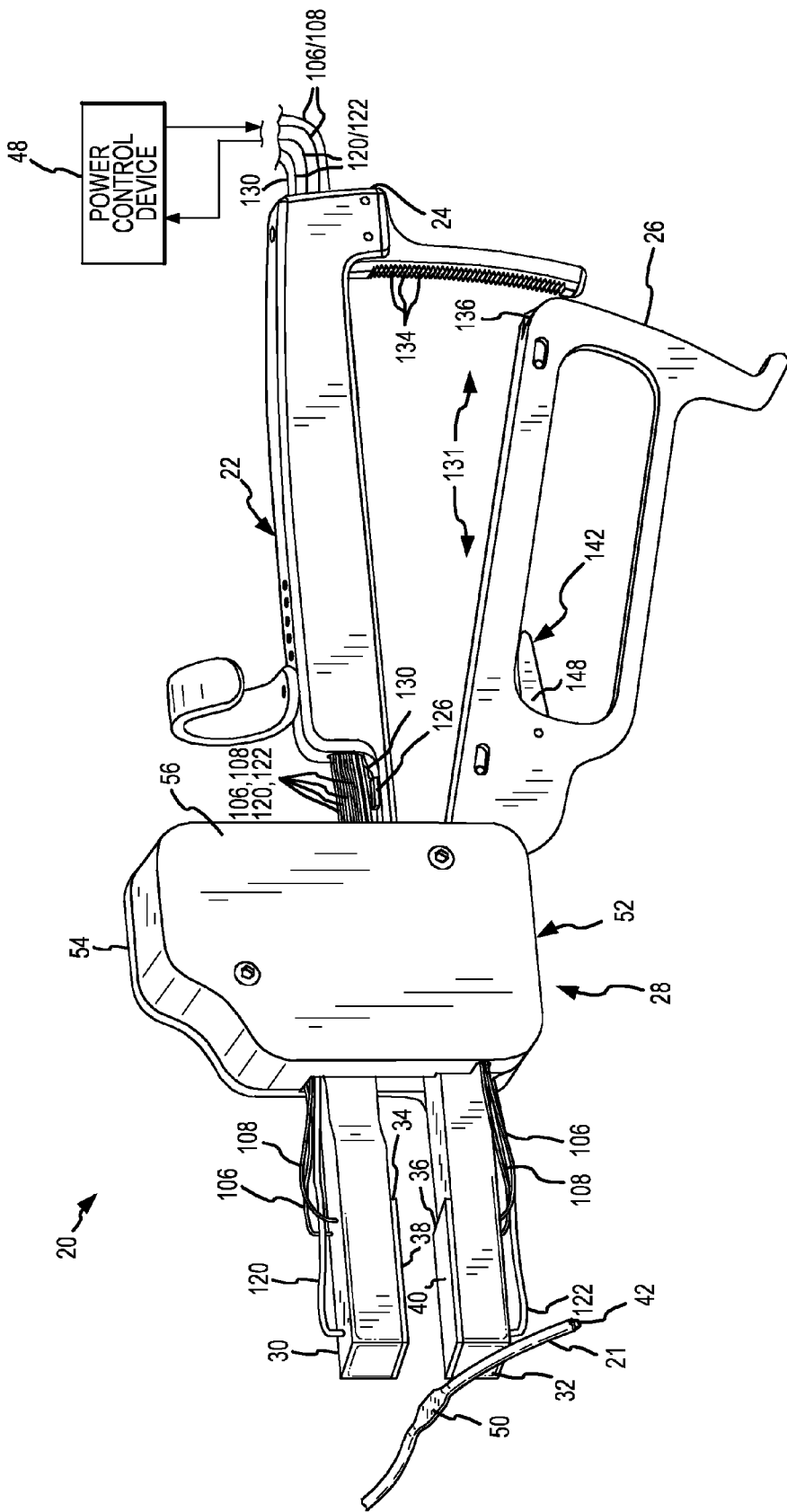
FIG. 5 is a perspective view of the tissue fusion apparatus shown in FIG. 1 after the vessel has been fused as shown in FIG. 4.
Figure 19:
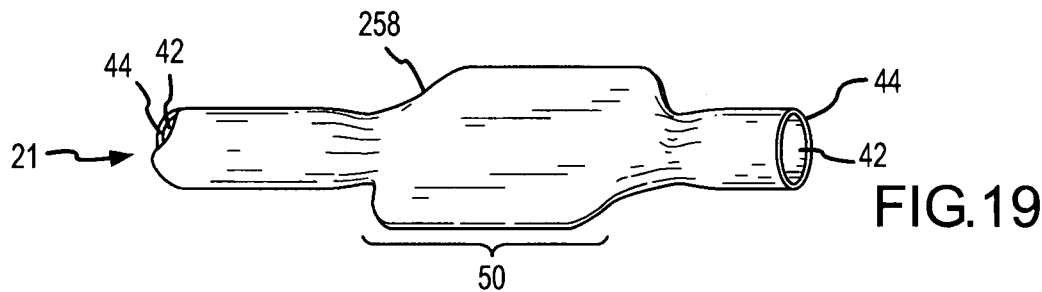
FIG. 19 is an enlarged partial perspective view of a sealed area of a vessel created as shown in FIGS. 4 and 5.

The heat denatures and disassociates the protein chains at the interface 46 of the apposite vessel walls 44 at the interface 46. The denatured protein chains immediately reconstitute or re-nature across the compressed tissue interface 46 to fuse or seal the vessel walls 44 together at a sealed area 50 (FIGS. 5 and 19). The sealed area 50 occludes the lumen 42 and prevents fluid normally confined within the lumen 42 from passing from the vessel 21. Immediately after the impulse of electrical power is terminated, the handles 24 and 26 are moved away from one another, which causes the arms 30 and 32 and the attached to jaws 34 and 36 to separate, releasing the vessel 21 as shown in FIG. 5. The tissue fusion procedure and seal is typically complete in 0.5 to 2.0 seconds.

The heat is disbursed substantially uniformly throughout the jaws 34 and 36 and across the compressed tissue interface 46 (FIG. 4) at the sealed area 50. The jaws 34 and 36 are formed of high thermal conductivity material, preferably ceramic material such as aluminum nitride, thereby achieving a substantially uniform temperature on the tissue squeezed between the working surfaces 38 and 40. The tissue interface temperature is approximately equal to the temperature of the jaws 34 and 36 due to the relatively thin amount of tissue compressed between the jaws.

The working surfaces 38 and 40 of the jaws 34 and 36 are smoothed or polished, preferably to an Ra of less than 0.15 microns. Jaws with working surfaces which have this degree of smoothness prevent the tissue from sticking to the jaws during fusion, despite the high relatively high temperature of the jaws against the tissue. By avoiding sticking, the integrity of the seal created is not damaged or its strength compromised from separating the jaws 34 and 36 after the seal has been formed, as would be the case if the tissue stuck to the jaws.

The impulse of electrical power delivered from the power control device 48 has a power density of at least 1000 Watts per square inch ($W/in^2$) (155 $W/cm^2$) and preferably greater than 1500 $W/in^2$ (233 $W/cm^2$) of the working surfaces of the jaws 34 and 36. This power density is considerably higher than the typical power density of 115-350 $W/in^2$ (18-54 $W/cm^2$) obtainable from a prior art RF tissue fusion device that is presently widely used The impulse of electrical power raises the temperature of the jaws at a preferable rate of about 500° C. per second. An impulse of electrical power of this magnitude is sufficient to increase the temperature of the jaws 34 and 36 to about 150° C. to 200° C. very quickly after application of the impulse. The fusion occurs over the 0.5-2.0 second preferred time duration of the electrical power impulse, allowing the jaws 34 and 36 to be separated or moved apart from one another to release the sealed area immediately after terminating the electrical power impulse.

The time required for achieving a reliable seal with high integrity against leaking is related to the amount of tissue squeezed between the working surfaces, the type of tissue involved and the temperature applied to the tissue. Larger vessels, thicker walled vessels or larger amounts of tissue typically require longer sealing times and/or higher temperatures. Effective seals on typical small to medium vessels of 2-3 mm diameter are achieved with electrical impulses of about 0.5 seconds duration, while seals of larger vessels in the neighborhood of 7-8 mm diameter are achieved with electrical impulses of about 2.0 seconds duration. Electrical impulses having a time duration of up to about 4.0 seconds are effective in some situations involving very large vessels, very thick walled vessels and/or lower temperatures.

Achieving consistent, reliable seals on a wide range of different sizes and types of vessels provides a significant procedural advantage over known prior art tissue sealing apparatus. Known prior art vessel sealing techniques are believed to require at least 5-12 seconds of power application before a seal is formed and the compressed vessel is released. Seals are accomplished with the present invention considerably more quickly compared to known prior art techniques. In addition, the seal created by the present invention has enhanced integrity and resistance to failure, compared to prior art seals, as described below.

The vessel 21 exemplifies biological tissue which is sealed with the present invention, and the lumen 42 of the vessel 21 exemplifies a lumen, duct, passageway, chamber or gap or separation which is to be permanently bonded, occluded, sealed, fused or joined. The actions of bonding, occluding, sealing, fusing or joining tissues are collectively referred to herein as fusion or sealing. In addition to the vessel 21, which may be an artery or a vein, other specific examples of biological tissue which may be fused or sealed include fallopian tubes, bile ducts, tissue surrounding an aveoli or air sac in the lung, the colon or bowel, or any other tissue where surgical ligation might be performed. In most but not necessarily all of the cases where tissue fusion or sealing is performed, the purpose of sealing or fusing the tissue is to confine a fluid or other bodily substance and its associated flow within a passageway which is either defined by or closed by fusing or sealing. Therefore, in accordance with a naming convention followed in this detailed description, the walls 44 of the vessel 21 are examples of apposite pieces of biological tissue which are fused or sealed, and the lumen 42 of the vessel 21 is an example of a passageway which is permanently occluded or closed or defined by sealing the apposite walls 44 at the interface 46 of the vessel 21.

The smoothness of the working surfaces 38 and 40 of the high thermal conductivity jaws 34 and 36 contributes to creating seals of high integrity in a short amount of time. Smooth working surfaces 38 and 40 release the fused tissue from the jaws 34 and 36 without sticking when the jaws separate (FIG. 5), despite the relatively high temperature of those jaws when compressing them against the tissue during tissue fusion. Preventing the tissue from sticking to the jaws as they separate avoids pulling the fused vessel walls apart, which could destroy or weaken the sealed area. Consequently, the fused interface of the vessel walls will have substantially all of the integrity and strength created by the fusion process, and that integrity and strength is not diminished by separation forces when the jaws separate. The smooth working surfaces 38 and 40 decrease the risk that the seal will ultimately fail.

Tissue sticking to the working surfaces of the heated jaws is a substantial problem in prior art tissue fusion devices. If the tissue sticks to the jaws as they separate, the integrity of the fused interface at the sealed area of the vessel will be compromised by the tendency to pull the sealed vessel walls apart at the fused interface 46. Even if the fused apposite vessel walls are not separated at the fusion interface, the separation force may weaken the walls enough to allow the natural fluid pressure within the lumen or passageway to eventually separate the vessel walls and create a leak.

Figure 4:
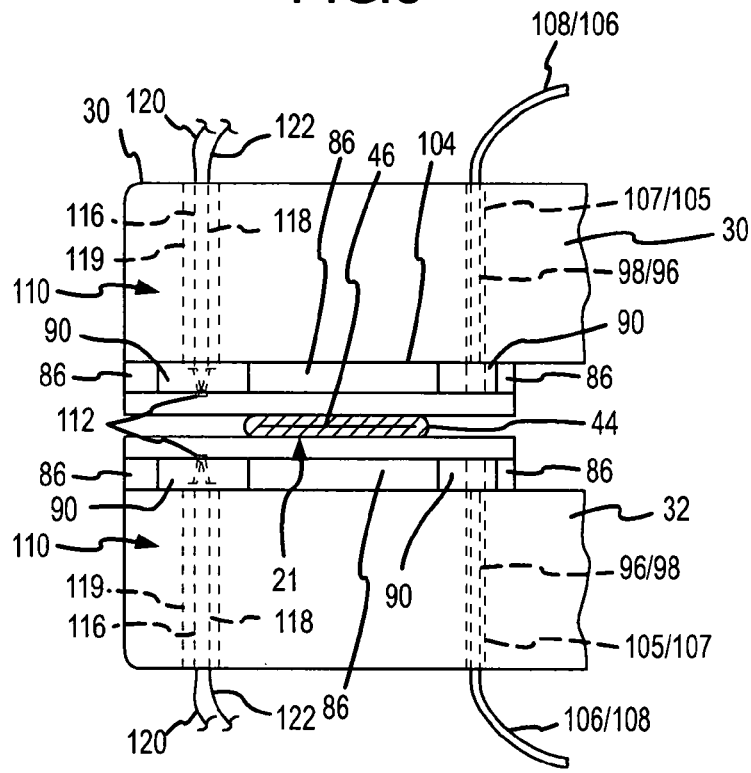
FIG. 4 is a view similar to FIG. 3, showing compression and fusion of the vessel.

Quickly achieving seals of high integrity is also facilitated by an even distribution of compression, force or pressure across the squeezed vessel walls 44 at the interface 46 (FIG. 4). The even force or pressure distribution across the tissue interface 46 is obtained by parallel movement of the working surfaces 38 and 40 toward one another when compressing the vessel 21 (FIG. 4). The parallel movement mechanism 28 causes the jaws 34 and 36 and their respective working surfaces 38 and 40 to move parallel to each other when opening and closing and compressing and releasing the vessel. The parallel movement of the jaws 34 and 36 avoids introducing shear forces on the sealed tissue interface 46 (FIG. 4) when the jaws separate. Shear forces have the effect of weakening the sealed tissue interface and diminishing the strength of the seal created.

Figure 6:
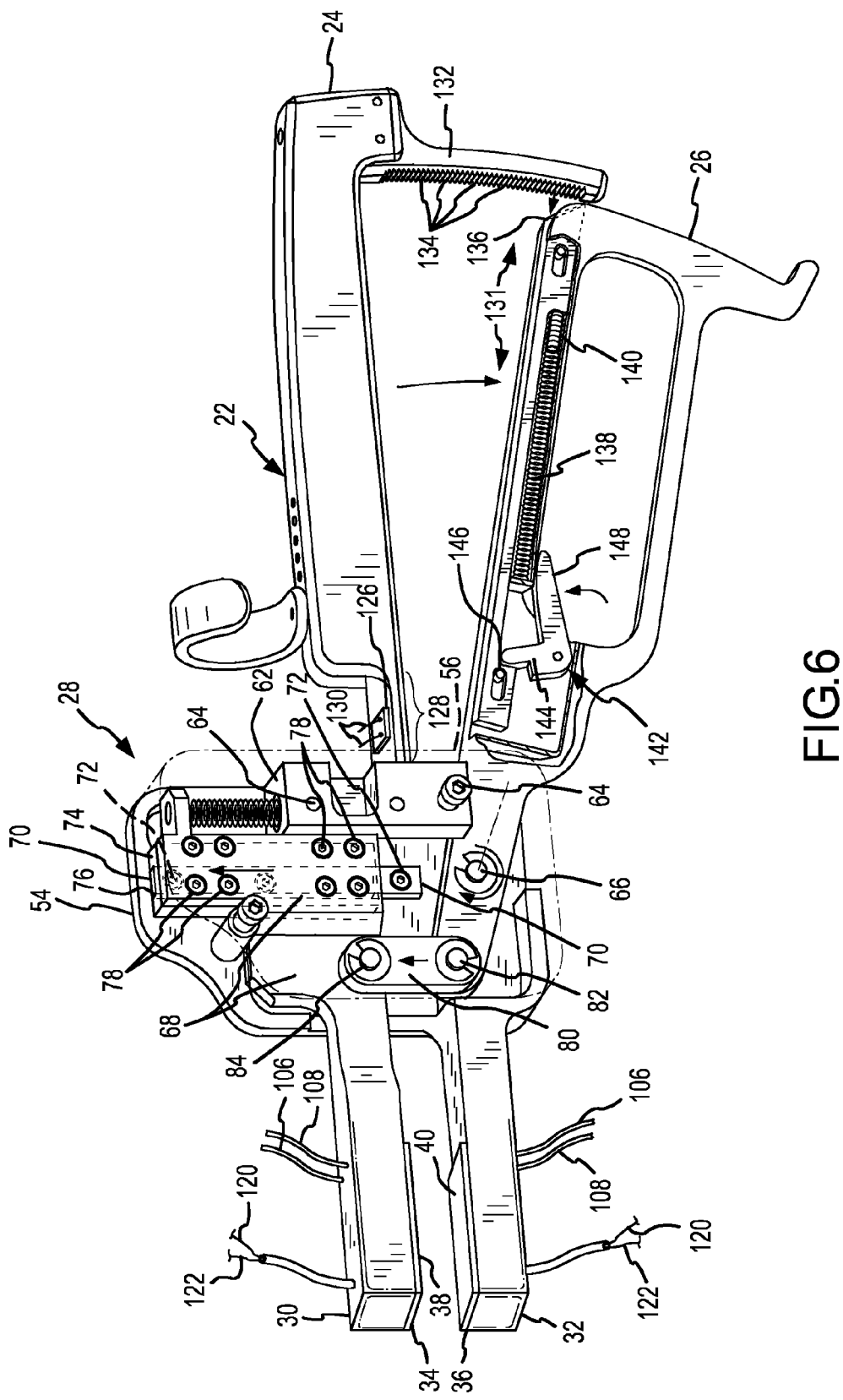
FIG. 6 is a perspective view of the tissue fusion instrument shown in FIGS. 1, 2 and 5, with portions broken away to show internal details of a parallel jaw movement mechanism and a handle locking and release mechanism, and with certain electrical conductors shown broken away.

Details of the parallel movement mechanism 28 of the instrument 22 are explained and shown mainly in conjunction with FIG. 6 but also in FIGS. 1, 2 and 5. The proximal handles 24 and 26 pivot with respect to one another in opening and closing movements. The parallel movement mechanism 28 transfers the force created by the opening and closing movements of the handles 24 and 26 into parallel opening and closing movement of the distal arms 30 and 32. The parallel opening and closing movement occurs, at a minimum, over the range of movement where the tissue is compressed between the working surfaces of the jaws during tissue fusion. The parallel movement avoids introducing adverse shear forces on the fused tissue and creates even force and pressure on the tissue when compressed.

The parallel movement mechanism 28 is enclosed within a housing 52 (FIGS. 1, 2 and 5). The housing 52 is formed by a rear wall member 54 and a front closure member 56 which includes integral top, bottom and side wall portions which enclose internal components of the parallel movement mechanism 28. Openings are formed in the integral side wall portions of the front closure member 56 to allow the handles 24 and 26 and the arms 30 and 32 to extend into the housing 52.

The top handle 24 is integrally attached at its distal end to a block 62, and the block 62 is rigidly attached to the rear wall member 54 by pins 64. The bottom arm 32 is formed integrally with the rear wall member 54. Thus, both the top handle 24 and the bottom arm 32 are rigidly connected relative to the rear wall member 54. Thus, the top handle 24 and the bottom arm 32 do not move relative to one another or relative to the rear wall member 54 or the housing 52. Only the bottom handle 26 and the top arm 30 and jaw 34 move relative to the stationary top handle 24 and the bottom arm 32.

The bottom handle 26 is pivotally connected to the rear wall member 54 at a pivot pin 66. The bottom handle 26 pivots around the pivot pin 66. When the top and bottom handles 24 and 26 are separated or moved toward one another, only the bottom handle 26 possesses the freedom to pivot. The pivot pin 66 is located slightly proximally from the distal end of the bottom handle 26.

The top arm 30 has a flange 68 integrally attached to its proximal end. The flange 68 extends generally parallel to the rear wall member 54. As the top arm 30 moves upward and downward, the flange 68 moves upward and downward with the top arm 30 within the housing 52 between the rear wall and front closure members 54 and 56.

A rail 70 is rigidly attached to the rear wall member 54 by pins 72. The rail 70 extends perpendicularly relative to the extension of the bottom arm 32. The rail 70 projects outward from the rear wall member 54 toward the flange 68. A guide block 74 is attached to the flange 68 by pins 78. The guide block includes a center channel 76 which conforms to the cross-sectional shape of the rail 70 and which movably receives and surrounds the rail 70. The size of the center channel 76 permits a slight clearance on each the three lateral sides of the rail 70 which extend outward from the rear wall member 54. The guide block 74, flange 68 and the attached top distal arm 30 are therefore movable along a path defined by the rail 70 and relative to the rear wall member 54.

The rail 70 is oriented perpendicularly to both the top and bottom arms 30, and therefore movement of the top arm 30 maintains the same parallel angular relationship with the bottom arm 32. The rail 70 has substantial structure to withstand the torque applied to the distal end of the top arm 30 during tissue compression to maintain the same relative angular relationship of the top arm 30 with the bottom arm 32.

One end of a link 80 is pivotally connected at the distal end of the bottom handle 26 by a pivot pin 82. The other end of the link 80 is pivotally connected to the flange 68 by another pivot pin 84. Upon the clockwise (as shown in FIG. 6) pivoting movement of the bottom handle 26 relative to the top handle 24, the distal end of the bottom handle 26 transfers upward force through the link 80 to the flange 68. The flange 68 moves upward along the rail 70, and causes the connected top arm 30 to separate from the bottom arm 32. Consequently, an opening movement of the bottom handle 26 relative to the top handle 24 causes an opening separation movement of the top arm 30 relative to the bottom arm 32. A gap or separation is created between the working surfaces 38 and 40 of the top and bottom jaws 34 and 36 by the separation movement of the bottom arm 32 relative to the top arm 30.

Closing the top and bottom handles 24 and 26 moves the distal end of the bottom handle 26 downward, causing the link 80 to move the flange 68 downward along the rail 70. The top arm 30 moves downward toward the stationary bottom arm 32, thereby closing the gap between the working surfaces 38 and 40 of the top and bottom jaws 34 and 36.

The movement of the top arm 30 is restricted by the orientation of the rail 70 and the guide block 74 which is connected to the flange 68. Because the guide block 74 can only move vertically as dictated by the rail 70, the flange 68 and the integrally attached top arm 30 can only move vertically as well. The vertical motion requires the parallel angular relationship of the top and bottom jaws 34 and 36 to remain constant as the top arm 30 opens and closes relative to the bottom arm 32.

The jaws 34 and 36 are attached to the top and bottom arms 30 and 32 so that the working surfaces 38 and 40 of the jaws 34 and 36 extend parallel with one another in a longitudinal dimension extending along the arms 30 and 32. The transverse dimension of the working surfaces 38 and 40 may also be planar with respect to one another (FIG. 11), but preferably one of the working surfaces has a slight convex or crowned shape (FIG. 12) while the other working surface is planar.

The parallel movement of the top and bottom arms 30 and 32 and the top and bottom jaws 34 and 36 allows the working surfaces 38 and 40 to apply and distribute force evenly across the compressed interface 46 (FIG. 4). The even force application is important to obtain even and uniform reconstitution of the denatured protein chains during fusion, resulting in enhanced strength and integrity of the sealed interface 46 (FIG. 4) and the sealed area 50 (FIG. 5). The parallel movement of the working surfaces 38 and 40 does not impart any shearing force on the sealed area 50 (FIG. 5) as the working surfaces 38 and 40 separate from one another. Such a shearing force could compromise the integrity of the fused interface 46 (FIG. 4), apart from whether the heated and compressed vessel 21 has any tendency to stick to the working surfaces of the jaws as they separate.

The mechanical advantage resulting from closing the handles 24 and 26, transferred through the parallel movement mechanism 28, moves the arms 30 and 32 and jaws 34 and 36 to compress the vessel 21 uniformly at each point on the interface 46 of the two apposite vessel walls 44 is sufficient to achieve a fully compressed and heated tissue thickness of from 0.05 mm to 0.10 mm. In general for jaws 34 and 36 with working surfaces which have a width of approximately 5 mm and a length of approximately 25 mm, the amount of force required is typically within the range of 110-150 N, although this force can vary considerably depending upon many factors, including the amount of tissue contacting the jaws, and the characteristics of the tissue. In order to achieve this range of compression, the parallel movement mechanism 28 must obtain an adequate mechanical advantage to transfer a comfortable amount of force applied on the handles 24 and 26 to the tissue. The force is related to the pressure between the working surfaces 38 and 40. The pressure is determined by the confrontational surface areas of the working surfaces 38 and 40 and the amount of force applied to the arms 30 and 32.

In a preferred embodiment, the working surfaces of the jaws have a length of about 25 mm and a transverse width of about 5 mm, creating an effective confrontational surface area of approximately 125 $mm^2$. The mechanical advantage must therefore be capable of producing a typical pressure of 0.88-1.2 Newtons per square millimeter ($N/mm^2$) with comfortable squeezing pressure on the handles 24 and 26. Producing a pressure of 0.88-1.2 $N/mm^2$ will assure a force of 110 N-150 N at each point of the compressed apposite tissue as it is fused. Because the pressure may vary according to the amount of tissue squeezed between the working surfaces 38 and 40, the force applied at each point to the two pieces of compressed tissue is a measure of the effectiveness of the compression necessary to achieve good tissue fusion. However, pressure must be considered to assure that an adequate amount of compression force is available to fuse the tissue.

Details of the jaws 34 and 36 are better understood by reference to FIGS. 3, 4 and 7-12. Each jaw 34 and 36 is essentially of the same structure and configuration. Each jaw 34 and 36 is preferably formed of a ceramic material with a high thermal conductivity, such as aluminum nitride. The jaws 34 and 36 are secured to the arms 30 and 32 with an adhesive, such as epoxy, which is applied in a layer 86 between the jaws 34 and 36 and the arms 30 and 32. Insulating spacers 90 are positioned near the distal and proximal ends of each of the jaws 34 and 36 between the jaws 34 and 36 and the arms 30 and 32. The adhesive layer 86 occupies the spaces between the spacers 90, the jaws 34 and 36 and the arms 30 and 32.

Figure 7:
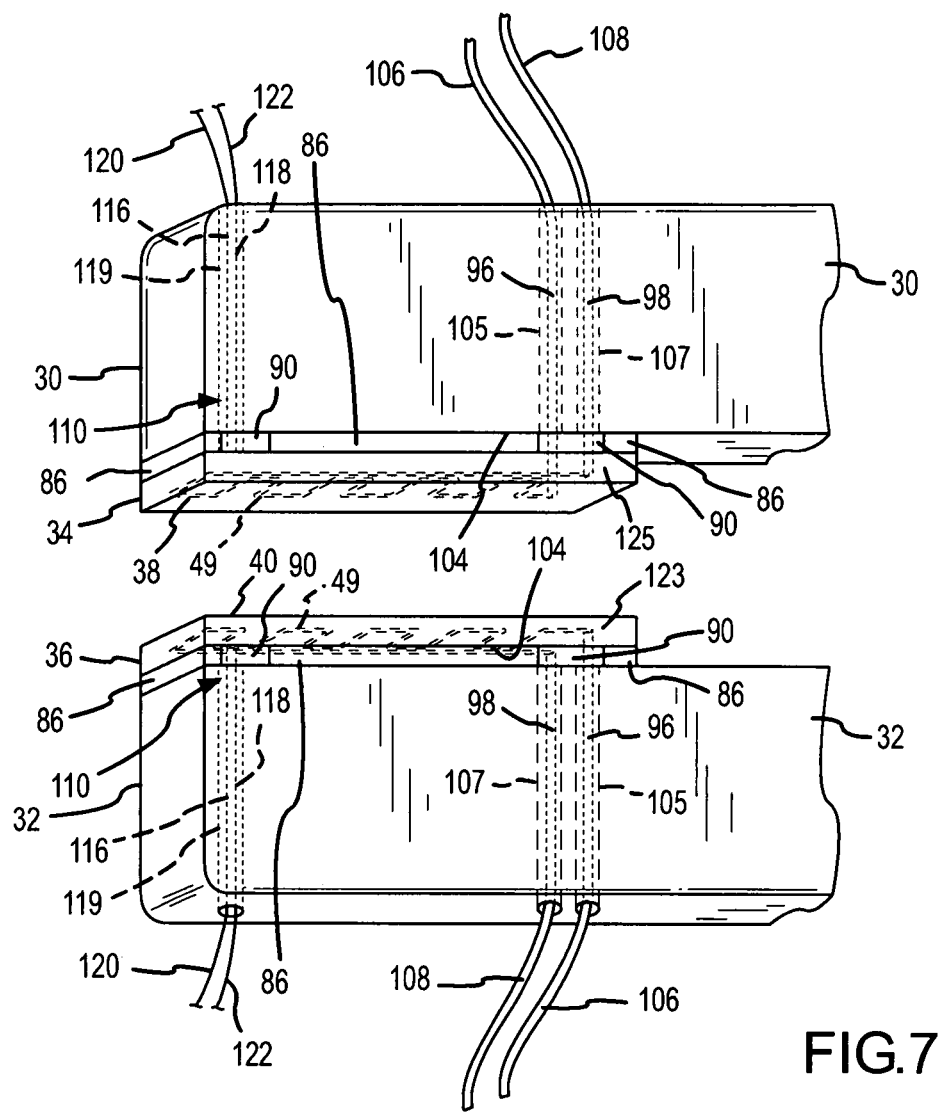
FIG. 7 is an enlarged partial perspective view of top and bottom distal arms and top and bottom jaws of the instrument shown in FIGS. 1-6.
Figure 8:
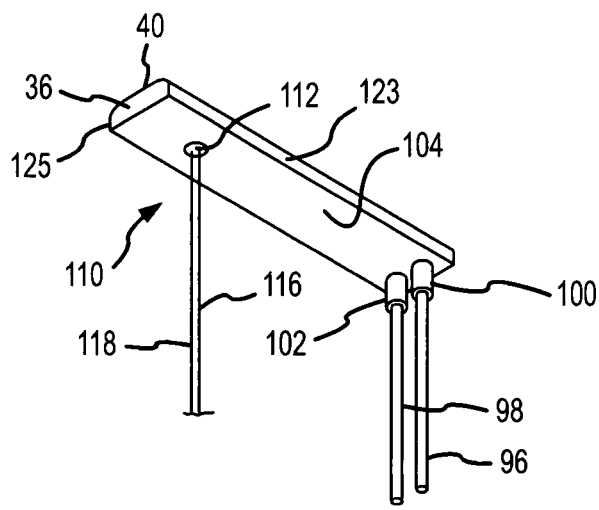
FIG. 8 is a perspective view of a bottom jaw shown in FIG. 7.
Figure 9:
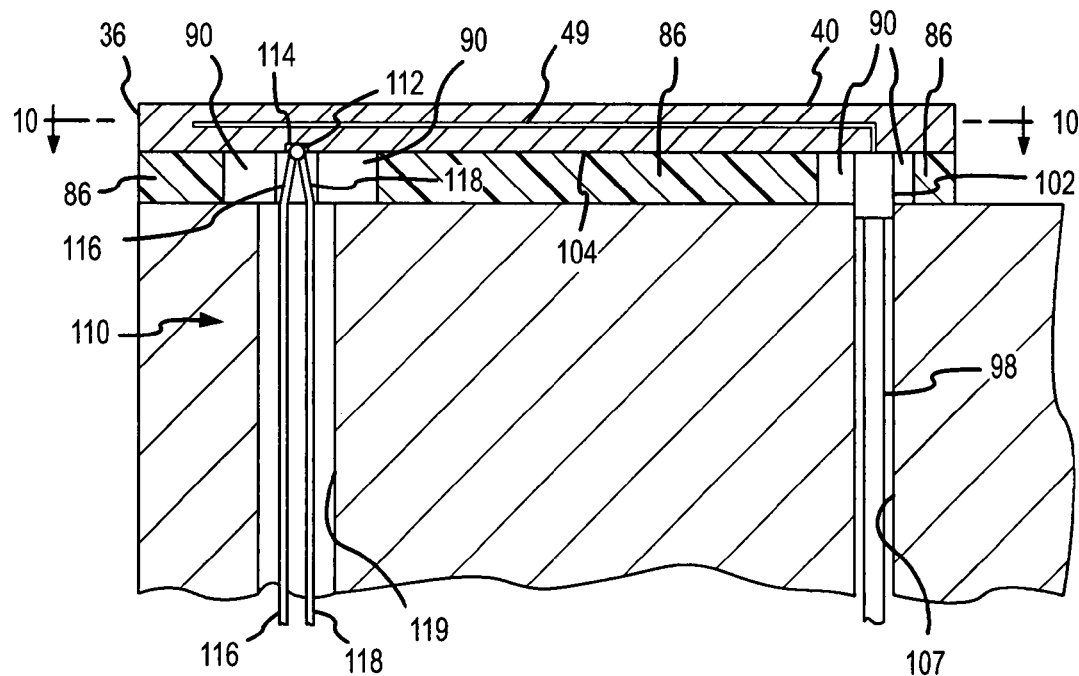
FIG. 9 is an enlarged longitudinal and vertical cross-sectional view of the bottom jaw shown in FIG. 7.
Figure 10:
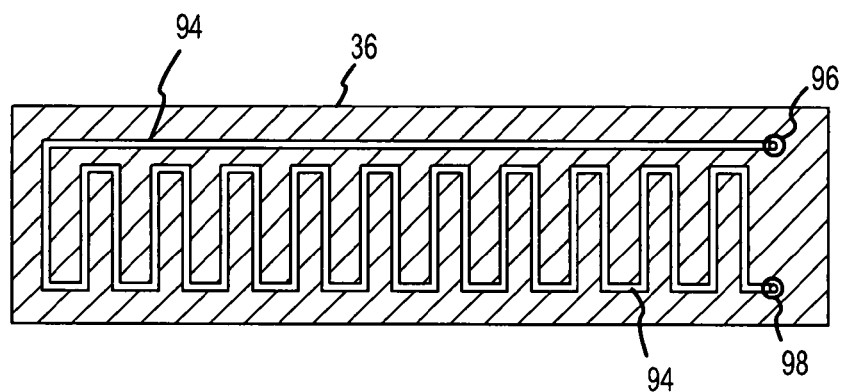
FIG. 10 is a transverse cross-sectional view of the bottom jaw shown in FIG. 9, taken substantially in the plane of line 10-10 shown in FIG. 9, and illustrating a heating element embedded in the bottom jaw.

The heating elements 49 are embedded in the ceramic material of the jaws 34 and 36, as shown in FIGS. 7, 9 and 10. The heating element 49 in each jaw 34 and 36 is essentially the same. Similarly, both jaws 34 and 36 are essentially the same, except with respect to the possibility of one or both of the jaws having a crowned working surface (FIG. 12). Because of the similarities, the heating element 49 and the jaw 36 are described in conjunction with FIGS. 8-12, with the understanding that the heating element 49 and the jaw 34 are the same.

The heating element 49 is formed by a length of an electrically conductive resistance material which produces heat when conducting electrical current. The heating element 49 has a high thermal shock withstanding capability and a high power density conducting capability. An example of one such electrically conductive resistance material which offers these capabilities is molybdenum. The heating element 49 extends substantially over the area of the jaw 36 (FIG. 10) so that heat is produced relatively uniformly throughout the jaw. The heat from the heating element 49 is conducted substantially uniformly through the jaw 36 due to the high thermal conductivity of the ceramic material from which the jaw 36 is formed, resulting in approximately equal temperature from point to point along the working surface 40 of the jaw 36.

Electrical wires 96 and 98 connect to opposite ends of the heating element 49. Electrical current is supplied to the heating element 49 through the wires 96 and 98. The wires 96 and 98 extend through shoulders 100 and 102 which are formed on a back side 104 of the jaw from the same ceramic material as the jaw 36. The shoulders 100 and 102 surround and support the wires 96 and 98 and hold them in position as part of the jaw 36. The ceramic material of the jaw 36 is an electrical insulator, thereby assuring that the current conducted through the wires 96 and 98 flows through the heating element 49 without short-circuiting to the arms 30 and 32 of the instrument 22 (FIG. 1).

To embed the heating element 49 within the jaw 36, enough powdered ceramic material to form the working surface 40 and the outer portion of the jaw 36 is placed in a mold and sintered. Thereafter, the heating element 49 is placed on this outer partially-formed jaw portion, preferably by using conventional fluid deposition techniques such as inking. More powdered ceramic material is then placed on top of the sintered outer portion of the jaw and the heating element 49 to form the remaining inner portion of the jaw including back side 104 and the shoulders 100 and 102. Thereafter, the powdered ceramic material which forms the inner portion of the jaw is sintered to form the ceramic inner portion of the jaw 36 while also sintering that inner portion of the jaw 36 to the previously-formed outer portion of the jaw 36, thereby completing the integral ceramic structure of the jaw.

In addition to embedding the heating element 49 within the jaw in the manner described, the heating element can also be embedded by following the described procedure but without sintering the outer portion until the inner portion has also been formed. A single sintering occurs with respect to both the outer and inner portions simultaneously to hold the heating, element in place.

The wires 96 and 98 are mechanically and electrically connected to the ends of the heating element 49 by drilling holes through the shoulders 100 and 102 until the holes contact the ends of the embedded heating element 49. The wires 96 and 98 are inserted through the holes until the ends of these wires contact the ends of the heating element 49. The ends of the wires 96 and 98 and the ends of the heating element 49 are permanently connected together by brazing in an oven. The wires 96 and 98 and the shoulders 100 and 102 therefore extend from the back side 104 of the jaw 36.

When the jaws 34 and 36 are attached to the arms 30 and 32, respectively, by the adhesive layer 86, the wires 96 and 98 extend through openings 105 and 107 which are formed in each of the arms 30 and 32 to receive the wires 96 and 98, as shown in FIGS. 7 and 9. The openings 105 and 107 are sufficiently large to avoid electrical contact with the wires 96 and 98, although the wires 96 and 98 are insulated in the areas within the openings 105 and 107. Conductors 106 and 108 connect to the ends of the wires 96 and 98. The conductors 106 and 108 from each jaw 34 and 36 extend through the housing 52 of the parallel movement mechanism 28 and along the top handle 24 to the power control device 48, as shown in FIGS. 1 and 2. The power control device 48 delivers the electrical current through the conductors 106 and 108 to the heating element 49 in each jaw 34 and 36, thereby heating the jaws.

The current supplied by the power control device 48 (FIGS. 1 and 2) is regulated relative to the temperature of the working surfaces 38 and 40 of the jaws 34 and 36. The temperature of each jaw is separately measured by a thermocouple 110 associated with each jaw, shown in FIGS. 3, 4, 7 and 9. The thermocouple 110 associated with each jaw 34 and 36 is essentially the same. Therefore, only one thermocouple 110 is described in association with the jaw 36 shown in FIG. 9, since the other thermocouple is substantially identical.

The thermocouple 110 comprises an electrical node or junction 112 of two dissimilar metal wires 116 and 118, as shown in FIG. 9. The junction of the two dissimilar wires 116 and 118 creates a conventional type JT/C thermocouple junction 112. A slight voltage is developed at the junction 112 by the inherent electrical characteristics of the two dissimilar metal wires 116 and 118, and the magnitude of that voltage varies in relationship to the temperature of the junction 112. Thus, the voltage developed at the junction 112 is related to the temperature of the junction 112. The wires 116 and 118 extend through an opening 119 formed in each arm 30 and 32 (FIGS. 3 and 4). The wires 116 and 118 may be insulated over that portion of their length which extends through the opening 119.

The voltage developed at the junction 112 is conducted through the wires 116 and 118 to conductors 120 and 122, which connect to the ends of the wires 116 and 118, respectively. The conductors 120 and 122 extend from the thermocouple 110 of each jaw 34 and 36 through the housing 52 of the parallel movement mechanism 28 and along the top handle 24 to the power control device 48, as shown in FIGS. 1 and 2. The voltage from the thermocouple 110, conducted through the conductors 120 and 122, is used by the power control device 48 as a feedback signal to control the amount of electrical current delivered through the conductors 106 and 108 and the wires 96 and 98 to the heating element 49 in the jaws 34 and 36, thereby independently regulating the temperature of the working surfaces of the jaws.

The thermocouple 110 is permanently thermally and mechanically attached to the jaw by oven brazing the junction 112 of the dissimilar metal wires 116 and 118 within a recess 114 formed into the ceramic material on the back side 104 of each jaw, as shown in FIG. 9. The attachment of the junction 112 to each jaw establishes good thermal conductivity of the junction 112 with each jaw, thereby enabling the junction 112 to respond to the temperature of the jaw. The high thermal conductivity material of each jaw distributes the heat from the heating element 49 throughout the jaw relatively rapidly. The temperature of the working surface of the jaw is typically slightly different from the temperature of the junction 112 because the junction 112 is not exactly at the working surface and slight dynamic thermal gradients exist within the jaw despite the high thermal conductivity of the jaw material. However, the temperature measured by the thermocouple junction 112 is closely correlated to the temperature of the working surface of the jaw, to result in temperature measurements which closely represent the temperature of the jaw working surface. Moreover, because the tissue compressed between the jaws during tissue fusion is relatively thin, the thermal transfer to the thin tissue causes that tissue to assume a temperature which is very close to the temperature of the jaw working surfaces.

Both of the working surfaces 38 and 40 may be flat and planar as shown in FIG. 11. In such circumstances the planar working surfaces are maintained in a parallel relationship with one another by the positioning of the jaws 34 and 36 on the arms and by the parallel movement of the arms 30 and 32. Longitudinal edges 124 of the jaws 34 and 36 are rounded or radiused to avoid imparting or concentrating pressure to the vessel 21 in such a way to weaken the vessel at the edge of seal formed.

A preferred alternative to the planar configuration of the working surfaces 38 and 40 is one flat planar working surface and a crowned working surface on the opposite jaw. Both working surfaces could also be crowned. A crowned working surface 40 is shown in FIG. 12. The working surface 40 possesses a slight outward convex shape when viewed transversely to the longitudinal dimension of the jaw 36, as shown in FIG. 12. The crowned or convex curvature of the working surface is useful for applying more force to the vessel at the center of the working surface, while simultaneously creating a slightly graduated variation in the extent of tissue compression from the center of the working surface to the longitudinal radiused edges 124. The slight variation in tissue compression is instrumental in achieving an optimal sealing force on the tissue squeezed between the working surfaces 38 and 40. However, in most cases, once adequate pressure is obtained, it is not necessary to achieve optimal pressure to accomplish adequate fusion with the present invention, so long as adequate force is available to obtain a fully compressed heated tissue thickness in the effective tissue fusion range, which for blood vessels is 0.05 mm to 0.10 mm.

The curvature of the crowned working surface 40 of the jaw is in the transverse direction across the working surface. The amount of curvature of the working surface 40, as shown in FIG. 12, is such that the radius of curvature of the working surface 40 in the transverse dimension is approximately 21 mm for a jaw which has a transverse width of approximately 5 mm. This radius of curvature generally causes the center of the crowned working surface to be approximately 0.1 mm higher than the working surfaces near the longitudinal edges 124 of the jaw 36, before those longitudinal edges 124 are radiused.

An important aspect of the present invention is that the working surfaces 38 and 40, and preferably side surfaces 123 and 125 (FIGS. 8, 11 and 12) and the radiused longitudinal edges 124 of the jaws 34 and 36, have a high degree of smoothness. A sufficiently high degree of smoothness is capable of preventing any sticking of the compressed and heated tissue to the jaws 34 and 36 after the vessel 21 has been sealed. The smoothness of the side surfaces 123 in 125 similarly prevents any overhanging tissue adjacent to the working surfaces 38 and 40 from sticking to the jaws 34 and 36 when the vessel 21 is sealed. Eliminating the occurrence of tissue sticking to the jaws is a substantial improvement in the field of tissue fusion because sticking tissue is responsible for destroying or substantially weakening the seal in a significant proportion of those incidents where the seals fail. Eliminating the occurrence of tissue sticking to the jaws also offers a substantial convenience to surgeons, because a considerable amount of time is consumed during the surgical procedure in cleaning the jaws of adhered tissue. By avoiding the necessity to clean the jaws, a time required to perform the surgical procedure is diminished, resulting in reduced risk and trauma to the patient.

The conventional measurement of smoothness is referred to as Ra. To achieve the degree of smoothness most desirable in accordance with the present invention, the working surfaces 38 and 40, the side surfaces 123 and 125 and the longitudinally radiused edges 124 of the jaws 34 and 36 are formed from a ceramic material, such as aluminum nitride, or a material having a surface microstructure like ceramic material, and such surfaces have an Ra of 0.15 microns or less. Jaws formed of aluminum nitride with surfaces having a smoothness represented by an Ra of 0.15 microns or less have been determined to result in no tissue sticking to the jaws after fusion has been completed and the jaws are separated.

For jaw surface smoothness in the Ra range of 0.15 to 0.40 microns, a spectrum of smoothness exists where the frequency of sticking increases in relation to decreasing smoothness, although the frequency of sticking is not in a linear relationship to decreasing smoothness. For a small increase in smoothness at the lower end of the range, a large reduction in the frequency of tissue sticking occurs. For an Ra of less than 0.15 microns, no sticking of the tissue has been observed, and the force required to separate the working surfaces from the vessel is not significantly different than if the vessel had not been present between the working surfaces. For an Ra range of 0.15 to 0.20 microns, sticking does not occur or only occurs with very minimal or virtually nonexistent frequency, and the force required to separate the working surfaces from the sealed vessel is not significantly greater than the force required to separate the working surfaces from the sealed vessel when the Ra is less than 0.15 microns. In the Ra range of 0.20 to 0.25 microns, sticking occurs with a slightly greater frequency, and the force required to separate the tissue from the working surfaces is slightly increased. In the Ra range of 0.25 to 0.40 microns, a moderate increase in the frequency of sticking occurs, and the force required to separate the tissue from the working surfaces is also moderately increased. Finally, in the Ra range of 0.40 to 0.50 microns, sticking becomes significantly more frequent and the force required to separate the tissue from the working surfaces is further increased. However, an Ra in the range of 0.40 to 0.50 microns provides less tissue sticking than with the known prior art jaws used for tissue fusion, or for jaws having an Ra of about 0.60 microns or greater.

The sticking of tissue described herein applies to that tissue upon which pressure has been applied from the working surfaces during tissue fusion. Sticking is not intended to apply to any tissue or fluid, such as blood, which remains on the working surfaces after the jaws have been separated and the sealed tissue is removed from the working surfaces. Although tissue and fluid may remain on the working surfaces after the tissue is removed, such tissue and dried fluid may easily be wiped from the working surfaces.

A conventional profilometer is used to measure the roughness of the working surfaces and to obtain the Ra values described herein. One example of such a commercially available profilometer is a Pocket Surf® portable surface roughness gauge manufactured by Mahr Federal, Inc. of Germany. Prior to measuring the roughness of the working surfaces, the profilometer was calibrated using a reference that had a known Ra. The Ra reference was certified against a known standard in accordance with ISO or ANSI standard procedures. The exemplary profilometer employed to obtain the Ra measurements described herein had an accuracy of ±0.05 microns and a resolution of 0.01 microns.

One useful ceramic material from which to form the jaws 34 and 36 is aluminum nitride. Aluminum nitride has a relatively high thermal conductivity of about 140-180 W/m° K. Aluminum nitride can also be polished to a smoothness of an Ra of 0.15 microns or less. When removed from the sintering oven after formation in a smooth mold, aluminum nitride can have an Ra as low as 0.60 microns, but not significantly lower. Working surfaces with an Ra of 0.60 microns appear smooth, but that apparent smoothness is above the acceptable range of Ra in accordance with the present invention.

Any polishing or other smoothing technique that can achieve the desired degree of smoothness of the working surfaces may be employed in accordance with the present invention. A satisfactory level of smoothness of the working surfaces of aluminum nitride jaws has been achieved by polishing the working surfaces using various grits of diamond paper or diamond pastes. Finer grades of abrasives were used in succession as the polishing proceeded toward the desired smoothness. The desired degree of smoothness was achieved by polishing the working surfaces by hand, successively using diamond grit paper with particle sizes of 6, 3, 1, 0.50, 0.25 and 0.10 microns in that order.

If the polishing is initiated with a grinding wheel or grit paper having a too coarse particle size, the working surface may be damaged and roughened to the extent that the desired smoothness can not be achieved when finer grits are used subsequently in the polishing process. When starting the polishing with too coarse of a particle size, the highest degree of smoothness (Ra of 0.15 microns or less) is difficult or impossible to achieve on aluminum nitride ceramic surfaces.

A strictly uniform smoothness across the working surfaces 38 and 40 is not required. Only those portions of the working surfaces 38 and 40 which contact the vessel 21 (FIG. 2) must be smoothed to the desired degree to obtain reduced tissue sticking. Thus, to the extent that the side surfaces 123 and 125 do not touch tissue, they may not require the same degree of smoothness as the working surfaces 38 and 40 and the longitudinal radiused edges 124.

The amount of force transferred from the working surfaces 38 and 40 of the jaws 34 and 36 to the vessel 21 is measured by a conventional strain gauge 126 attached to a section 128 of the top proximal handle 24, shown in FIG. 6. The section 128 of the top handle 24 has a reduced cross-sectional area. The strain gauge 126 is attached to extend longitudinally along the reduced cross-sectional area section 128. Attached in this manner, the strain gauge 126 measures the amount of deflection of the section 128 created by the force resulting from squeezing the handles 24 and 26 together. The extent of deflection of the section 128 is accurately correlated to the amount of force applied from the distal arms 30 and 32 to the tissue squeezed between the working surfaces 38 and 40 (FIG. 4). The signals from the strain gauge 126 are conducted through two conductors, collectively referenced 130, to the power control device 48, where those force-related signals are used to create a display of the force imparted to the compressed tissue and to control the power control device 48.

A handle locking and release mechanism 131 is connected to the proximal ends of the handles 24 and 26, as shown mainly in FIG. 6, and also in FIGS. 1, 2 and 5. The handle locking and release mechanism 131 includes a curved extension 132 with ratchet teeth 134 that extends downward from the proximal end of the top handle 24. The bottom handle 26 includes a ratchet pawl 136 that extends rearward from the proximal end of the bottom handle 26. The ratchet pawl 136 is connected to a rod 138 which extends longitudinally within the interior of the bottom handle 26. A spring 140 is connected between a proximal end of the rod 138 and a shoulder 141 of the bottom handle 26. The spring 140 is compressed and normally biases the rod 138 in the rearward direction. The normal rearward bias from the spring 140 on the rod 138 extends the ratchet pawl 136 rearward from the proximal end of the bottom handle 26.

When the handles 24 and 26 are squeezed together, the ratchet pawl 136 slides by and engages the individual ratchet teeth 134 in succession, until the handles 24 and 26 reach a squeezed-together position where the desired amount of force is applied on the compressed vessel 21. The handles can not separate or open because the ratchet pawl 136 is engaged with the ratchet teeth 134, thereby allowing the working surfaces 38 and 40 to maintain force on the compressed vessel 21 during fusion. The handle locking and release mechanism 131 allows an adequate and substantial amount of force or pressure to be maintained on the vessel 21 during fusion without requiring the surgeon to continually squeeze the handles 24 and 26. The handle locking and release mechanism 131 also prevents the force or pressure on the compressed vessel from substantially decreasing during the fusion procedure. The interaction of the ratchet pawl 136 with the ratchet teeth 134 prevents the handles 24 and 26 from moving apart from their squeezed-together position, until the ratchet pawl 136 is separated from the ratchet teeth 134.

The handle locking and release mechanism 131 includes a trigger 142 which, when squeezed, separates the ratchet pawl 136 from the ratchet teeth 134 and thereby allows the handles 24 and 26 to open with respect to one another. The trigger 142 includes a contact arm 144 which contacts and interacts with a shoulder 146 at the distal end of the rod 138. The normal bias from the spring 140 on the rod 138 biases the shoulder 146 against the contact arm 144, and causes the trigger 142 to assume the normal position shown in FIG. 2, with a release arm 148 of the trigger 142 extending generally parallel with the elongated dimension of the bottom handle 26. To disengage the ratchet pawl 136 from the ratchet teeth 134, the trigger 142 is squeezed which causes the release arm 148 to pivot counterclockwise as shown in FIG. 6. The counterclockwise movement of the contact arm 144 against the shoulder 146 moves the rod 138 in the distal direction, as shown in FIG. 6, and the distal movement of the rod 136 releases the engagement of the ratchet pawl 136 with the ratchet teeth 134. With the ratchet pawl 136 released from the ratchet teeth 134, the handles 24 and 26 are free to move away from one another.

The following example illustrates the utility of the smooth working surfaces 38 and 40 in vessel fusion. In a six-hour laboratory experiment, seals were formed on 101 samples of in vivo porcine tissue that included arteries, veins, tissue bundles, and mesentery. The tissue fusion instrument used in the experiment had aluminum nitride jaws which had been hand polished to an Ra of about 0.15 microns as determined by at least five measurements over the working surfaces. The aluminum nitride ceramic jaws had a width dimension of 5 mm and a length dimension of 25 mm and a thickness dimension of 1.5 mm. One of the working surfaces was crowned (FIG. 12) and the other working surface was flat or planar (FIG. 11). Each sample of tissue was compressed between the jaw working surfaces with a force of 110-150 N, resulting in a fully squeezed heated tissue thickness of about 0.05-0.10 mm for blood vessels. An impulse of power having a power density of 1500 W/in$^2$ (233 W/cm$^2$) was delivered by the power control device 48 (FIG. 1) to the heating elements in the jaws. The power impulse had a 2.0 second time duration. The impulse produced enough thermal energy to successfully seal the tissue in each of the 101 instances. The thermocouples of the jaws recorded peak temperatures of the jaw working surfaces of about 150-180° C. during the impulse.

After each seal was formed, the jaws were separated to release the fused tissue. The tissue was considered stuck to one of the working surfaces if the fused tissue did not separate itself immediately from the working surface which contacted the tissue. Of the 101 tissue samples fused in the experiment, none adhered to the working surfaces of the jaws using this sticking evaluation criteria. Moreover, on occasion, blood or other tissue was present on the working surfaces of the jaws before the tissue sample was compressed between the jaws. Even in these adverse situations, the tissue did not stick to the smooth working surfaces. The blood or other tissue initially present on the jaws adhered to the tissue sample fused, thereby producing clean working surfaces, but there was no adherence between the fused tissue and the smooth working surfaces. Use of the present invention subsequent to this experiment has also confirmed the non-stick performance of the polished working surfaces.

Figure 13:
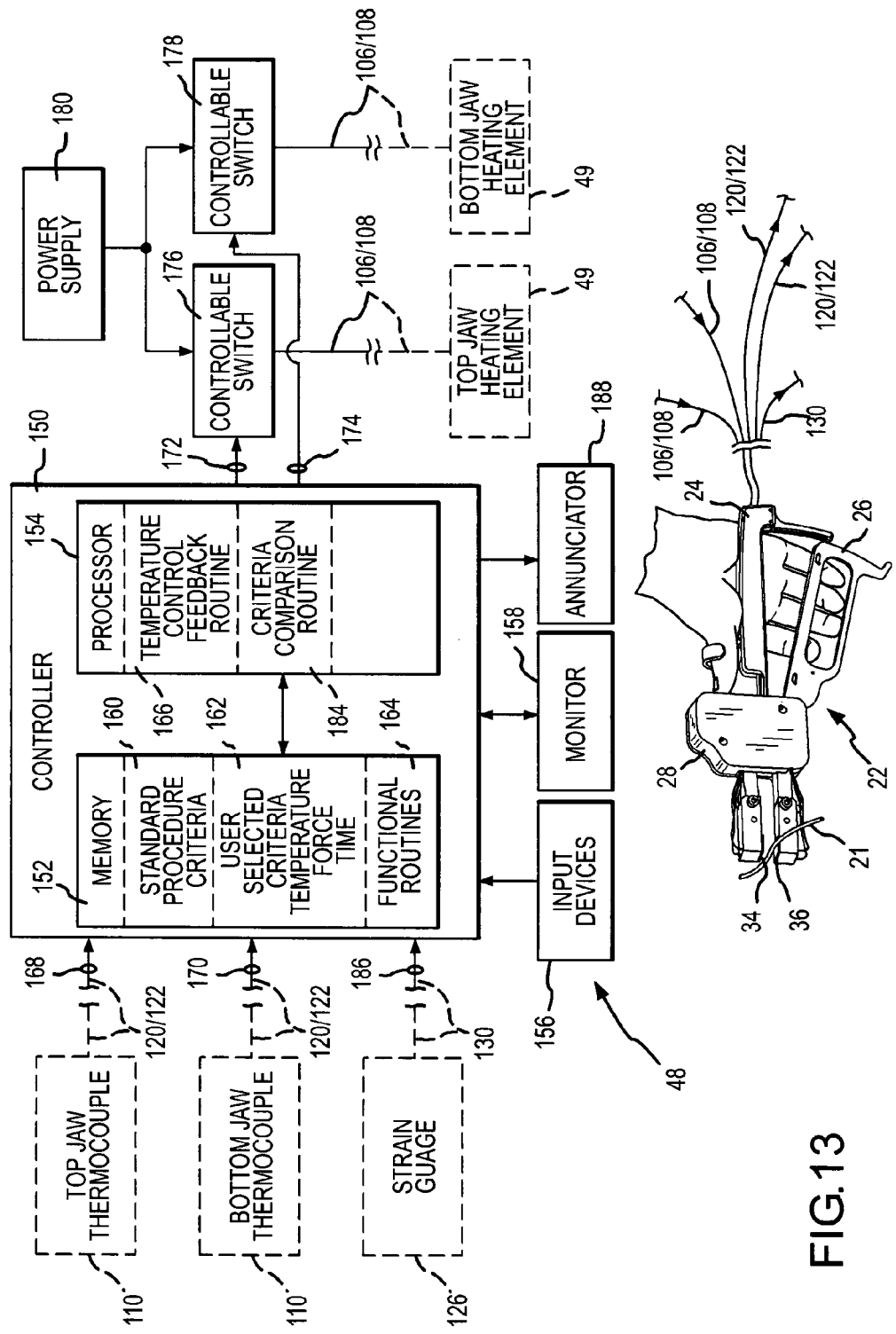
FIG. 13 is a more detailed block diagram of the power control device shown in FIG. 1, showing in block form certain aspects of the tissue fusion instrument shown in block diagram form in FIG. 1.
Figure 14:
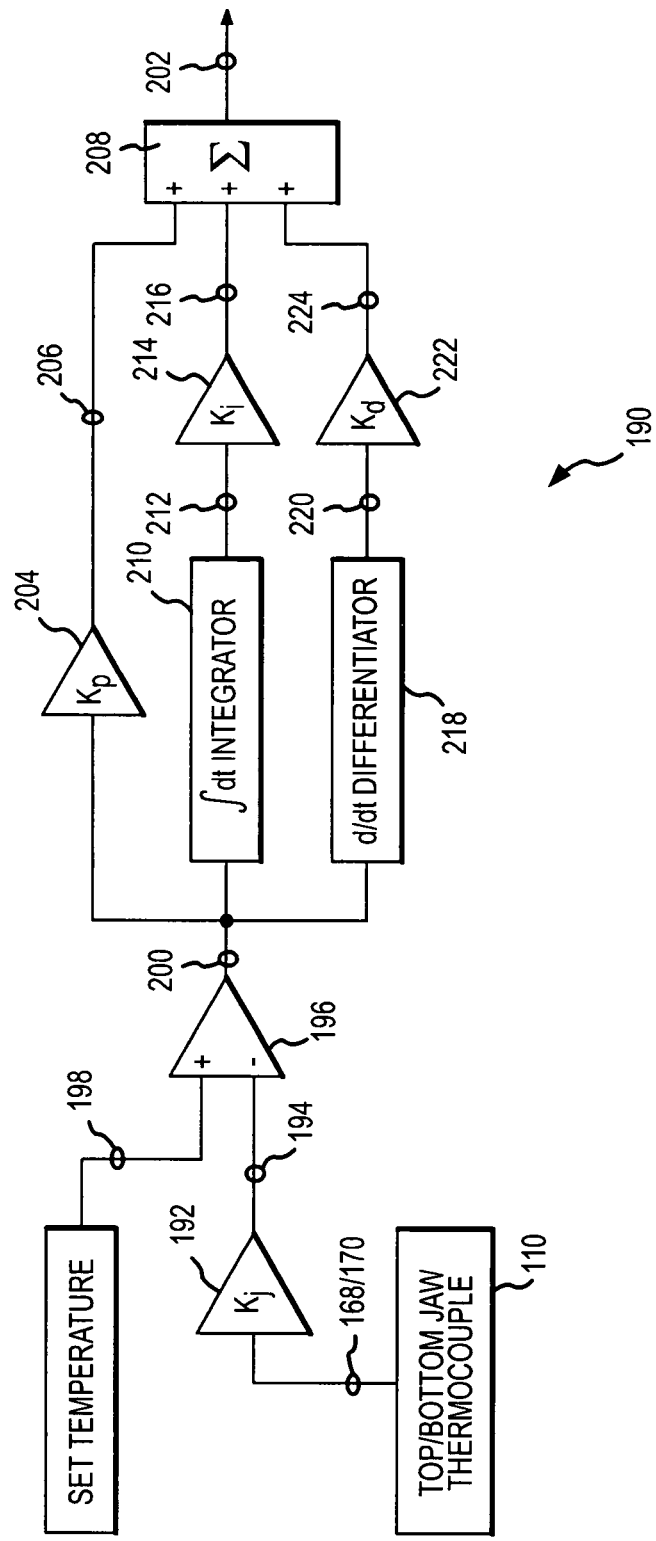
FIG. 14 is a block diagram illustrating the functionality of a temperature control feedback routine executed by a processor of a controller of the power control device shown in FIG. 13.

More details concerning the power control device 48 are shown in FIGS. 13-14. As shown in FIG. 13, the power control device 48 includes a controller 150 which includes a memory 152 and a processor 154. The memory 152 stores data and information supplied by conventional input devices 156 and/or supplied from a touch screen (not shown) of a conventional monitor 158. The information stored in the memory 152 includes criteria 160 which establish the parameters for one or more standard tissue fusion procedures. The standard procedure criteria 160 includes information describing the temperature to be attained at the working surfaces 38 and 40 of the jaws 34 and 36 of the instrument 22, the amount of force to be applied by the jaws 34 and 36 to the vessel 21 or other tissue during the procedure, and the amount of time during which electrical power is to be delivered to heat the jaws 34 and 36 to perform the procedure.

In addition, the memory 152 stores certain user-selected criteria 162 which can be used in place of some or all the standard procedure criteria 160 to accomplish tissue fusion. The ability to select and alter the criteria 162 allows the user to adjust the fusion criteria to the surgeon's preferences or to perform procedures which may be better accomplished by using user-selected criteria rather than standard criteria.

The memory 152 also stores the instructional code which defines certain functional routines 164. The functional routines 164 cause the processor 154 to control the power delivered to the jaws 34 and 36. The functional routines 164 also contain control constants and gain factors that are used when the processor 164 executes certain functional routines, as illustrated by the examples described below.

One of the functional routines executed by the processor 154 is a temperature control feedback routine 166. The temperature control feedback routine 166 is executed in response to temperature signals 168 and 170 obtained from the sensing of the temperatures of the top jaw 34 and the bottom jaw 36 by their respective thermocouples 110 (FIG. 9) and supplied over the conductors 120 and 122. The processor 154 responds to the individual temperature signals 168 and 170 from each of the top and bottom jaws 34 and 36 and separately regulates the amount of electrical power supplied to each top and bottom jaw heating element 49. In doing so, the processor 154 executes the same temperature control feedback routine 166 for each jaw 34 and 36, thereby separately regulating the temperature of each jaw 34 and 36. In most cases, it is desired that the temperatures of both jaws 34 and 36 be the same during the procedure, but different amounts of electrical power may be required to cause each jaw 34 and 36 to attain and maintain the desired temperature, due to different thermal loads imposed by different physiology of the tissue or vessel 21 contacted by each jaw 34 and 36.

The processor 154 creates switching signals 172 and 174 which are supplied to conventional controllable switches 176 and 178, such as solid-state relays. In response to the switching signals 172 and 174, the controllable switches 176 and 178 conduct electrical power from a conventional adjustable low-voltage, high-current direct current (DC) power supply 180 to the heating element 49 of the top jaw 34 and to the heating element 49 of the bottom jaw 36.

By separately controlling the characteristics of the switching signals 172 and 174, the conductivity characteristics of the controllable switches 176 and 178 are also separately varied to separately control the amount of electrical power delivered to each heating element 49 of the top and bottom jaws over the conductors 106 and 108. In this manner, the amount of electrical power, and consequently heat available at each of the jaws 34 and 36, is varied independently in each jaw.

The processor 154 also executes a criteria comparison routine 184. The criteria comparison routine 184 utilizes the temperature signals 168 and 170 from the top and bottom jaws and a force signal 186 supplied over the conductors 130 from the strain gauge 126, as well as internally generated time duration information which is measured from the time that the impulse of electrical power is applied to the jaws 34 and 36. Execution of the comparison routine 184 creates information which is presented on the monitor 158 as graphs or other presentations of the temperature signals 168 and 170, the force signal 186 and the elapsed time. The temperature of each jaw 34 and 36 may be displayed separately on the monitor 158, while the force and the time are presented singularly with respect to each separate fusion procedure.

Execution of the comparison routine 184 also compares the temperature signals 168 and 170, the force signal 186 and the elapsed time to corresponding limits or values of the temperature, force and elapsed time established by the standard procedure criteria 160 or by the user-selected criteria 162 for the tissue fusion procedure. The result of comparing the actual temperatures, force and elapsed time to the procedure criteria limits or values is information which is supplied to the monitor 158 and/or an annunciator 188. Execution of the comparison routine 184 identifies if and when the actual operative values associated with the tissue fusion procedure fall outside of the procedure criteria limits or values. Under circumstances where the actual operative values achieve or deviate from the established procedure criteria values, visual and/or audible signals are delivered from the annunciator 188, and related signals may also be presented visually on the monitor 158.

For example, execution of the comparison routine 184 establishes the time instant at which electrical power impulse is delivered to the jaw heating elements. The comparison routine 184 monitors the force signal 186 to determine when the vessel 21 has been compressed sufficiently to apply the electrical power impulse for heating the jaws 34 and 36. A certain force limit must be exceeded by squeezing the handles 24 and 26 before the controller 150 recognizes that a tissue fusion procedure is underway. Once the initial force limit value is attained, the controller 150 delivers the control signals 172 and 174 to the controllable switches 176 and 178 to apply electrical power to the heating element 49 of the top and bottom jaws, thereby heating the working surfaces of the jaws 34 and 36. Simultaneously, the comparison routine 184 begins timing the time duration at which the electrical power is delivered at the selected temperature for the procedure.

As another example of the execution of the comparison routine 184, once it is recognized that the temperature of the working surfaces 38 and 40 of the jaws 34 and 36 has reached the selected temperature, a signal is delivered from the annunciator 188. Under circumstances where one or both of the top and bottom jaw temperatures exceed or fall below the temperature limits, or under circumstances where the force between the jaws 34 and 36 has not reached the desired final level or exceeds or falls below the desired final level, an out-of-criteria signal is delivered from the annunciator 188. Such limit information may also be presented on the monitor 158 as well, and is used by the surgeon during use of the instrument 22.

A temperature feedback power control routine 166, which offers the well-known and significant advantage of predictive capability, is a proportional, integral, derivative (PID) computation, represented in functional block diagram form shown in FIG. 14 by a temperature control feedback circuit 190. The PID temperature control feedback circuit 190 is shown as interconnected individual functional devices, but the PID functionality represented by the circuit 190 may also be executed by the instructional code executed by the processor 154 of the controller 150 (FIG. 13).

The temperature signal 168 or 170 supplied by the top or bottom thermocouple 110 of jaw 34 or 36 (FIG. 14) is multiplied in an amplifier 192 by a scaling factor Kj which converts the value of the temperature signal 168 or 170 from the jaw itself to a scaled temperature signal 194. The scale temperature signal 194 represents the temperature of the working surface of the jaw. The application of heat to the jaw from the heating element 49 (FIG. 10) causes slightly different temperatures at different locations in the jaws. A slight temperature gradient within the jaws causes the temperature at the working surfaces to be different from the temperature at other locations within the jaws, including the temperature at the location which is sensed by the thermocouple 110, despite the fact that the jaws are made from high thermal conductivity material. Accordingly, the temperature sensed by the thermocouple is not typically equal to the temperature of the working surface of the jaw which contacts the vessel being sealed. The scaling factor Kj is used to convert the actual thermocouple-sensed temperature signal 168 or 170 to the scaled temperature signal 194, by multiplying the scaling factor Kj and the actual thermocouple-sensed temperature signal 168 or 170. The result is that the scaled temperature signal 194 closely approximates the actual temperature of the working surface of the jaw.

The value of the scaling factor Kj is developed empirically, under conditions where the walls 44 of the vessel 21 are contacted and squeezed between the jaws. To empirically develop the value of Kj, it is necessary to conduct an actual temperature measurement of the jaw working surface, which can be accomplished by using conventional infrared temperature measurement techniques, for example. The actual temperature measurement is then related to the temperature measurement from the thermocouple to obtain the scaling factor Kj.

The scaling factor Kj may be different depending upon the desired temperature of the working surface of the jaw during the procedure. For example, the selection of a lower working surface temperature for the tissue fusion procedure may result in a lower value for the scaling factor Kj compared to the scaling factor applicable when a higher working surface temperature is selected for a different tissue fusion procedure. The values of the scaling factor Kj are stored in the memory 52 as part of the standard procedure criteria 160 (FIG. 13).

The amplifier 192 supplies a scaled temperature signal 194 to a negative input terminal of a comparator 196. A set temperature signal 198 is supplied to the positive input terminal of the comparator 196. The set temperature signal 196 represents the desired temperature of the working surfaces of the jaws which is to be attained and maintained during the tissue fusion procedure. The set temperature signal 196 is one of the standard temperature criteria 160 or the user-selected temperature criteria 162 stored in the memory 152 (FIG. 13).

The comparator 196 subtracts the scaled temperature signal 194 from the set temperature signal 198, and the result is an error signal 200. The error signal 200 represents the difference between the actual temperature of the working surfaces of the jaw (signal 194) and the desired or set temperature of the working surfaces of the jaws for the procedure (signal 198). It is the error signal 200 and the elapsed time that cause the predictive aspects of the proportional, integral and derivative functionality to create a control error signal 202 which will be used by the processor 154 to create the switching control signals 172 and 174 (FIG. 13). The switching control signals 172 and 174 regulate the temperature of the working surfaces 38 and 40 of the jaws 34 and 36.

The proportional aspect of the PID functionality is achieved by multiplying the error signal 200 by a proportional constant Kp in an amplifier 204. A proportionalized error signal 206 is created by the amplifier 204 and is supplied to one input terminal of a summer 208. The value of the proportional constant Kp is established through selection of the standard criteria 160 or the user-selected criteria 162 stored in the memory 152 (FIG. 13).

The integral aspect of the PID functionality is achieved by integrating the error signal 200 in an integrator 210. The integrator 210 supplies an integrated error signal 212 which is then multiplied in an amplifier 214 by an integration constant Ki to create an adjusted integrated error signal 216. The adjusted integrated error signal 216 is applied to another input terminal of the summer 208. The value of the integration constant Ki is established through selection of the standard criteria 160 or the user-selected criteria 162 stored in the memory 152 (FIG. 13).

The differential aspect of the PID functionality is achieved by differentiating the error signal 200 in a differentiator 218 to create a differentiated error signal 220. The differentiated error signal 220 is then multiplied in an amplifier 222 by a differentiation constant Kd to create an adjusted differentiated error signal 224. The differentiated error signal 224 is applied to a third input terminal of the summer 208. The value of the differentiation constant Kd is established through selection of the standard criteria 160 or the user-selected criteria 162 stored in the memory 152 (FIG. 13).

Although the differentiator 218 is shown as receiving the error signal 200, it is also possible for the differentiator 218 to respond to the scaled temperature signal 194. Under such circumstances, the differentiation of the scaled temperature signal 194 results in a higher value of the signal 220. Under these circumstances the value of the differentiation constant Kd is adjusted to represent the changed value of the signal 220.

The proportionalized error signal 206, the adjusted integrated error signal 216 and the adjusted differentiated error signal 224 are summed together in the summer 208. The result of the addition is the control error signal 202. The values of the proportional constant Kp, the integration constant Ki and the differentiation constant Kd are all selected to achieve the desired predictive capability resulting from the contribution of the proportionalized, integrated and differentiated error signals 206, 212 and 220 in creating the control error signal 202. Adjusting the values of the PID constants Kp, Ki and Kp in this manner allows the error signal 202 to achieve the desired degree of control to heat the jaws.

The values of the proportional constant Kp, the integration constant Ki and the differentiation constant Kd are different based upon the desired set temperature and the time for the fusion procedure. The amount of force applied during the fusion procedure may also have an effect on the value of the PID constants Kp, Ki and Kd, although that impact will generally be less than the effect from the desired temperature and time duration of the fusion procedure.

The values of the PID constants Kp, Ki and Kd may remain constant throughout the delivery of power during the course of a single procedure, or they may also be varied during the delivery of power in a single procedure. For example one set of PID constants may be used when increasing the temperature of the working surfaces of the jaws to the desired set temperature, and another set of PID constants may be used to maintain the temperature of the working surfaces at the desired set temperature during the tissue fusion procedure. The criteria comparison routine 184 executed by the processor 154 (FIG. 14) substitutes the different proportional constants into the temperature control feedback routine 166 and the temperature control feedback circuit 190 according to the temperature of the jaw working surfaces, the elapsed time of the power impulse, and to a lesser degree, the force applied. All of the values of the PID constants are stored in the memory 152 (FIG. 13).

In response to the control error signal 202, the power control device 48, shown in FIGS. 13 and 14, delivers an impulse of electrical power which is sufficient to raise the temperature of the working surfaces of the jaws from room temperature to a sealing set point temperature of about 150° C. to 200° C. at a rate greater than 150° C. per second and preferably greater than 500° C. per second. The rate should be as high as possible without creating untoward side effects on the tissue. Of course, the power control device 48 also has the capability of maintaining the selected temperature for the time duration of the power impulse, which is preferably about 0.5 to 2.0 seconds but which may extend to approximately 4.0 seconds. In general, the impulse of power begins with the switching signals 172 and 174 causing the controllable switches 176 and 178 to deliver DC current from the power supply 180 until the temperature of the jaws approaches the set point temperature. Thereafter the switches 176 and 178 are turned on and off to maintain the set point temperature during the fusion procedure. In general the on-time decreases and the off time increases to maintain the set point temperature after it is initially achieved. Delivering the impulse of power is effective to quickly establish and maintain a set point temperature creates a strong and effective seal.

To achieve these temperatures, a power density of about at least 1000 W/in$^2$ (155 W/cm$^2$) and preferably greater than 1500 W/in$^2$ (233 W/cm$^2$) is required, with higher power densities required to achieve shorter sealing times and to seal larger vessels. However, the power density is not always an accurate representation of the capability of raising and maintaining the working surfaces of the jaws at the desired tissue fusion temperature. The thermal load created by the compressed vessel is variable, and thus directly influences the power density. Moreover, the distal arms 30 and 32 of the instrument 22 (FIG. 1), the wires 96 and 98 and the conductors 106 and 108 connected to the jaw heating elements 49 (FIG. 12) and the dissimilar wires 116 and 118 of the thermocouple 110 and conductors 120 and 122 connected to the thermocouples 110 (FIG. 7) act as heat sinks to transfer thermal energy away from the jaws, thereby making it difficult to account accurately for the amount of energy delivered to the vessel 21 and that amount of energy dissipated to the instrument 22. As a consequence, the temperature of the working surfaces of the jaws is a better indication of the important thermal variable for fusing tissue.

The temperatures of the working surfaces 38 and 40 must be sufficiently high to denature the collagen fibers at a temperature of about 60-70° C. and also high enough to denature the elastin fibers at a temperature of about 120° C., and to quickly obtain enough dehydration of the compressed tissue to achieve good reconstitution of the denature proteins chains before the tissue becomes too dehydrated to permit good fusion. By delivering an impulse of power that can heat the working surfaces of the jaws to temperatures in the range of 150° C. to 200° C. and maintaining that sealing temperature for a preferable time duration of from about 0.5 to 2.0 seconds while the vessel is compressed to a thickness of about 0.05 to 0.10 mm, the collagen and elastin fibers are first denatured and then reconstituted across the interface 46 to create a strong seal.

Because the electrical power is delivered for a short period of time, the heat generated by this power does not diffuse appreciably into the surrounding walls of the vessel.

As a result, the walls adjacent to the seal remain substantially unaffected by thermal energy spread. The strength and capability of the adjacent tissue is not compromised to the point where it may contribute to a failure of the seal.

Figure 15:
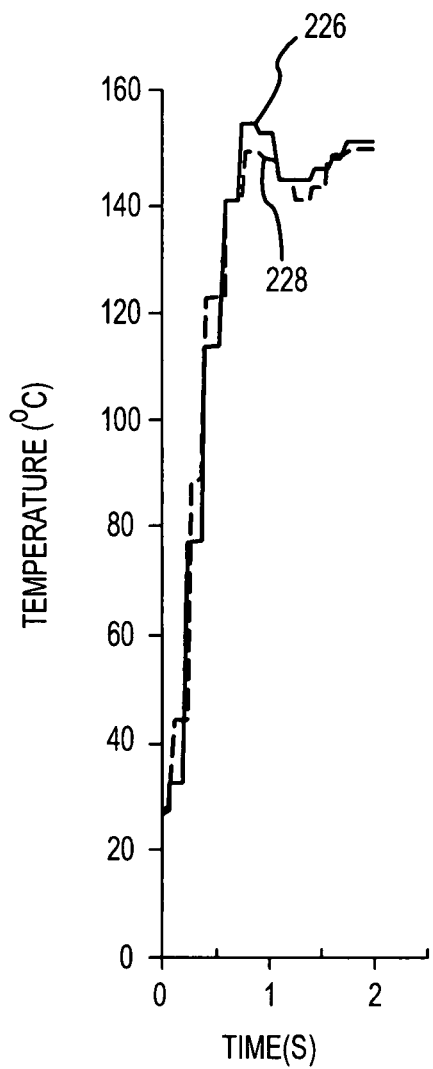
FIG. 15 is a graph of temperature versus time illustrating the temperature of jaws of the tissue fusion instrument when sealing a vessel with a 2.0 second time-duration impulse of electrical energy.

Sealing a vessel with an impulse of electrical power which elevates the temperature of the working surfaces to a set temperature of approximately 150° C. and maintains that 150° C. sealing temperature for a time of about 2.0 seconds is illustrated by the graph shown in FIG. 15. The temperature of the working surface on the upper jaw is referenced at 226, and the temperature of the working surface of the lower jaw is illustrated at 228. The temperatures in the upper and lower jaws are comparable to one another, due to the independent and rapid temperature control feedback of the controller 150 (FIG. 13).

The electrical power is applied by the controller to the jaw heating elements beginning at the 0.0 time reference. The energy applied for an initial ramp up time increases the temperature of the working surfaces for approximately 0.7 seconds, at which time the temperature of the jaw working surfaces is approximately at the desired 150° C. set point temperature for the tissue fusion procedure. Thereafter, between approximately 0.7 seconds and 2.0 seconds, the controller 150 manages the delivery of electrical power to maintain the temperature of the jaw working surfaces at the set point temperature of about 150° C. A slight amount of temperature overshoot and undershoot occurs immediately after the transition from the initial temperature ramp-up to the desired set point temperature, but that slight oscillation of temperature is within an acceptable range of the desired set point temperature.

After the delivery of power is stopped at 2.0 seconds, the impulse of electrical power is terminated and the jaws are opened immediately thereafter to release the vessel. The annunciator 188 or the monitor 158 (FIG. 13) indicates when the jaws can be opened to release the vessel. After the vessel is released from the jaws, the sealed area 50 (FIG. 5), which has been compressed to a width of about 0.05-0.10 mm, lacks substantial mass to retain heat and cools rapidly when exposed to air. The jaws also quickly cool in the air after release of the tissue, but that cooling is not material to the invention and is therefore not shown in FIG. 15.

Figure 16:
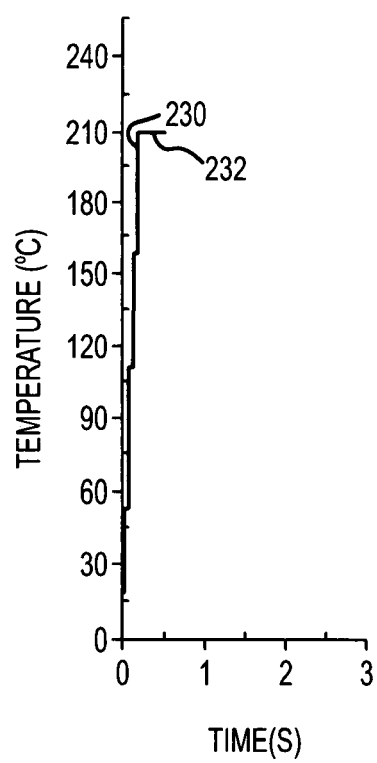
FIG. 16 is a graph similar to FIG. 15, illustrating the temperature of the jaws of the tissue fusion instrument when sealing a different vessel with a 0.5 second time-duration impulse of electrical energy.

Sealing a vessel with a 0.5 second impulse of power which achieves a jaw working surface temperature of approximately 200° C. is illustrated in FIG. 16. Each of the top and bottom jaw working surface temperatures are separately referenced at 230 and 232. The temperature rapidly increases from 0.0 seconds to the set temperature of about 200° C. in slightly more than 0.2 seconds. Thereafter, the delivery of electrical power to the jaw heating elements is controlled to maintain the working surface temperature at about 200° C. until 0.5 seconds have elapsed since the commencement of delivering the electrical power impulse. At that time, the electrical impulse is terminated and the jaws are opened to release the vessel. Again, the sealed area, which has a thickness of 0.05-0.10 mm for blood vessels, cools rapidly upon being exposed to the air. The jaws also quickly cool in the air after release of the tissue, but that cooling is not material to the invention and is therefore not shown in FIG. 16.

At temperatures of 150° C. to 200° C., the time duration of the power impulse must be relatively short to avoid damaging, destroying or substantially weakening the vessel. For example, maintaining the temperature of approximately 200° C. for 5.0 seconds has the effect of so dehydrating the tissue between the working surfaces of the jaws so that it becomes friable and brittle. Such characteristics make the sealed area prone to break and develop a leak.

The staircase nature of the curves 226, 228, 230, and 232 shown in FIGS. 15 and 16 result from a digital sampling routine of the PID controller. The discrete sampling points observed in FIGS. 15 and 16 are separated by significant amounts of time, but higher sampling frequencies are possible. Increasing the rate of sampling by the PID controller allows for better system control over such variables as overshoot and rise time.

The strength and integrity of the seals created by use of the present invention have been evaluated using burst tests. To evaluate the strength of the seal with a burst test, the lumen of the vessel is connected to a source of pressurized fluid, such as air, which inflates the vessel adjacent to the sealed area until a rupture or burst in the sealed area or the vessel wall occurs. The fluid pressure at the rupture point is measured, and the rupture pressure represents the strength of the seal. The test is repeated many times with different specimens of sealed tissue. A sufficient number of burst tests are conducted to achieve a statistically significant number of samples by which to evaluate the strength and integrity of the seals. The burst tests indicate that the seals formed have some range of variability in strength, and the seal strength is dependent upon the type and the size of the vessel sealed. Despite the variations in the seal strength, the burst pressures observed indicate that the seals formed have more than sufficient strength to reliably withstand the applicable physiological pressures, and in most cases, multiples of those pressures.

In addition to having a statistically higher and more consistent burst pressure, the typical failure mode of a seal made in accordance with the present invention is also substantially different from the edge-seal leak or mid-seal wall leak failure modes of seals made by use of the typical, known prior art tissue fusion devices which are presently in significant use. Typical edge-seal or mid-seal wall leaks are illustrated in FIGS. 17 and 18, respectively.

Figure 17:
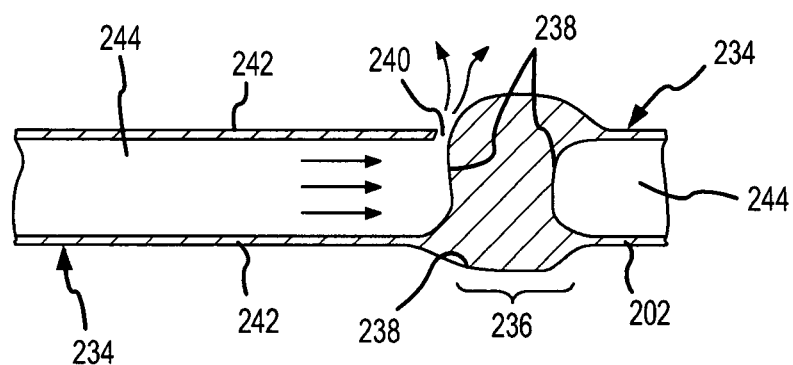
FIG. 17 is a longitudinal cross-sectional view of a partial vessel which has been sealed with a prior art technique, viewed orthogonal to a flat surface of the sealed area of the vessel, illustrating an edge-seal leak.

As shown in FIG. 17, a vessel 234 has been sealed at area 236 by a typical prior art technique. The view of FIG. 17 is orthogonal to the relatively large flat surface of the sealed area 236. An edge 238 of the sealed area 236 delineates its boundary. An edge-seal leak occurs at location 240 when the edge 238 of the sealed area 236 ruptures through a wall 242 of the vessel 234 at a location adjacent to the sealed area 236, under the influence of pressure applied in the lumen 244 on the left-hand side of the vessel (as shown). Usually the edge-seal leak 240 results from the application of excessive heat and compression concentrated at the edge 238 or over the entire sealed area 236, or as a result of RF arcing which impacts the wall 242 of the vessel 234 and weakens the vessel at or near the edge 238. The edge 238 may also be weakened by excessive compression from non-parallel jaws of a handpiece or from a shearing action on the tissue at the sealed area when separating the jaws, as described above. The edge-seal leak 240 diverts fluid from the lumen 244 to the outside of the vessel 234.

Figure 18:
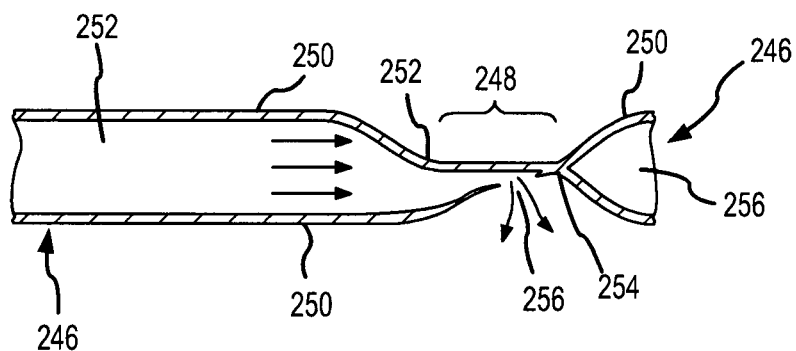
FIG. 18 is a longitudinal cross-sectional view of a partial vessel which has been sealed with a prior art technique, viewed parallel to flat surfaces of the sealed area of the vessel, illustrating a mid-seal wall leak.

The typical mid-seal wall leak is illustrated in FIG. 18 where a vessel 246 was previously sealed at an area 248 by a typical prior art technique. The view of FIG. 18 is parallel to the flat surfaces of the sealed area 248. The sealed area 248 was formed by compressing and fusing apposite walls 250 of the vessel 246. Unsealed vessel walls 250 extend away from edges of the sealed area 248. Under the influence of pressure applied in the lumen 252 on the left-hand side of the vessel 246 shown in FIG. 18, the sealed wall portions of the sealed area 248 have started to separate due to the fluid pressure against the sealed area 248. A remaining portion 254 of the sealed area 248 remains intact with the walls of the vessel sealed together. A mid-seal wall leak 256 occurs when the separated vessel wall of the previously sealed area 248 ruptures at 256 and allows fluid to flow from the lumen 252 to the exterior of the vessel 246.

Both edge-seal leak 240 (FIG. 17) and mid-seal wall leak 256 (FIG. 18) create difficult medical problems. Usually, the sealed areas have enough initial integrity to withstand the pressure of the fluid in the lumen of the vessel for a short amount of time, but continued blood or fluid pressure variations within the body cause the edge-seal leak or the mid-seal wall leak to occur at a later time, usually after closure of the surgical incision and completion of the entire surgical procedure. Post operative internal bleeding will have severe consequences if the bleeding is not stopped quickly. Consequently, both an edge-seal leak 240 and a mid-seal wall leak 256 require undertaking a second surgical procedure to stop those leaks. Such second surgical procedures following immediately on the earlier procedure induce considerable additional trauma and risk to the patient.

The failure mode of seals created by use of the present invention, if failure occurs, is substantially different from the prior art edge-seal leak 240 and the mid-seal wall leak 256 shown in FIGS. 17 and 18. Practical use of the present invention within its defined and preferred parameters has never resulted in an edge-seal leak or a mid-seal wall leak, after creating many hundreds of seals. On a fundamental level, an edge-seal leak 240 or a mid-seal wall leak 256 results because the strength of at least part of the sealed area is greater than the strength of a part of the vessel adjacent to or within the sealed area, usually as a result of the adjacent vessel part or the sealed part being damaged during the tissue fusion procedure. The failure mode of the seals created by the present invention is considerably different, because the strength of the vessel adjacent to the sealed area is not impacted to the point where the strength of the sealed area is significantly less than the strength of the vessel adjacent to the sealed area. The failure mode created by the present invention may be characterized as a mid-seal separation, and the mid-seal separation is of considerably less risk than either the edge-seal leak 240 or the mid-seal wall leaks 256, for the reasons discussed below.

Figure 20:
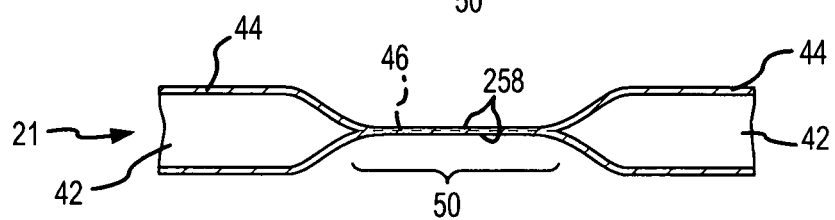
FIG. 20 is a longitudinal cross-sectional view of the partial vessel shown in FIG. 19, taken in a plane substantially perpendicular to a flat surface of the sealed area.

The mid-seal separation available from the present invention, if such a separation occurs at all, is illustrated in FIGS. 19-23. As shown in FIGS. 19 and 20, the vessel 21 is sealed at the sealed area 50 according to the present invention. The sealed area 50 is formed by forcing portions 258 of the walls 44 of the vessel 21 into apposition with one another at the tissue interface 46 and by delivering heat to the compressed apposite portions 258 of the walls 44 at the interface 46. The temperature of the vessel wall portions 258 is sufficient to denature and coagulate the protein chains in the wall portions 258 at the interface 46 and then allow those denatured proteins chains to re-nature and reconstitute to form the high-integrity sealed area 50. The fusion of the wall portions 258 at the tissue interface 46 occludes the lumen 42 of the vessel 21.

Figure 21:
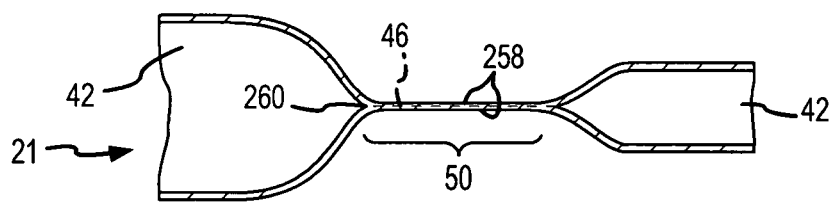
FIG. 21 is a longitudinal cross-sectional view of the partial vessel shown in FIG. 20, with increased fluid pressure applied in the vessel on a left-hand side of the sealed area.

After fusion of the wall portions 258 at the interface 46 in the sealed area 50, the application of fluid pressure within the lumen 42 on the left-hand side of the sealed area 50 causes the vessel 21 to expand as shown in FIG. 21. The walls 44 of the vessel 21 stretch and balloon outward from an edge 260 of the interface 46. A characteristic of the seal created by the present invention is that the strength of the fusion at the interface 46 between the wall portions 258 at the sealed area 50 is less than the strength of the unsealed walls 44 of the vessel 21 and is also less than the strength of the portions 258 of the wall after they have been fused together at the sealed area 50. Even though the strength of the wall portions 258 after sealing may be somewhat diminished as a result of the heat and pressure application, the strength of those wall portions 258 is still greater than the strength of the fusion between the wall portions 258 at the interface 46, and the strength of the fused wall portions 258 at the interface 46 is still considerably greater than the normal amount of pressure applied within the lumen 42 by normal physiological events. These characteristics achieve a seal of substantial integrity which is capable of withstanding fluid pressures which are considerably greater than normal, as shown in FIG. 21, but which also provides safety and reliability if the sealed area 50 should experience a mid-seal separation.

Figure 22:
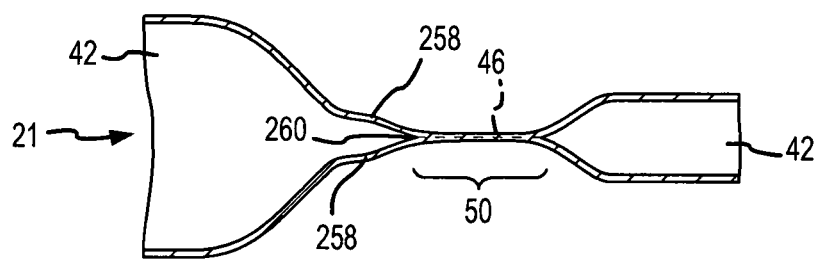
FIG. 22 is a longitudinal cross-sectional view of the partial vessel shown in FIG. 21, with greater fluid pressure applied in the vessel on the left-hand side of the sealed area and illustrating initiation of mid-seal separation of the sealed area.
Figure 23:
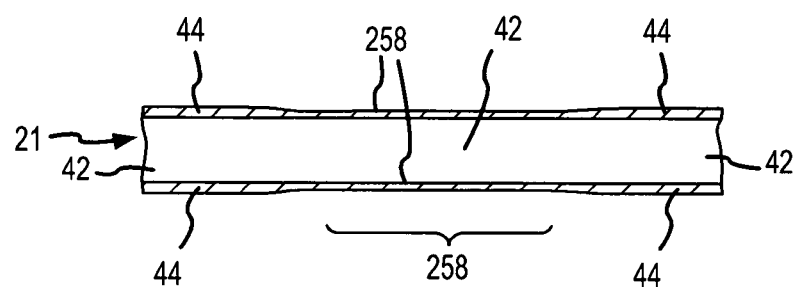
FIG. 23 is a longitudinal cross-sectional view of the partial vessel shown in FIG. 22, illustrating complete mid-seal separation of the sealed area.

If the fluid pressure applied within the lumen is increased beyond the exaggerated level shown in FIG. 21, the fused apposed wall portions 258 at the interface 46 began to separate from one another at the edge 260 without rupturing the vessel walls 44 adjacent to the sealed area 50 and without rupturing the separated wall portions 258 which had previously been fused together at the sealed area 50, as shown in FIG. 22. The pressure causes the sealed area 50 to experience a mid-seal separation, meaning that the previously-fused wall portions 258 separate at the interface 46. The pressure may continue to separate the previously-fused, apposed wall portions 258, with the separation continuing longitudinally along the interface 46. The separation may continue along the interface 46 until the entirety of the previously-fused wall portions 258 have separated, at which point the occlusion of the vessel 21 is eliminated and the vessel 21 opens completely as shown in FIG. 23.

Because the previously-fused wall portions 258 retain substantial natural strength as a result of the present invention, a rupture through the wall 44 of the vessel 21 is avoided. The entire sealed area 50 will separate in the manner shown in FIG. 23 in unusual circumstances, but neither the unaffected walls 44 nor the previously sealed wall portions 258 rupture to the exterior of the vessel 21 and create a leak from the lumen 42 to the exterior of the vessel, as is the case in a prior art edge seal leak 240 (FIG. 17) or a prior art mid-seal wall leak 256 (FIG. 18). The fluid-confining lumen 42 remains intact to confine the fluid within the vessel 21. Thus, even if the wall portions 258 at the sealed area 50 separate, such a mid-seal separation does not result in a rupture of the vessel wall 44 to permit fluid to flow from the lumen 42 to the outside of the vessel 21. The capability of sealing vessels in such a way to achieve a consistent and reliable mid-seal separation as a failure mode is thought to never before have been achieved from electrosurgical or electrothermal tissue fusion.

Figure 24:
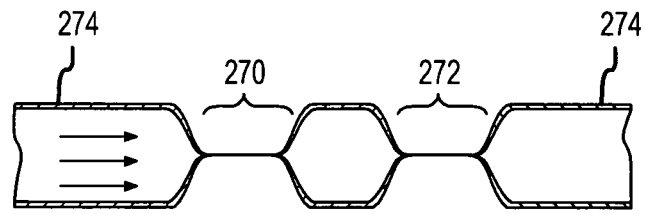
FIG. 24 is an enlarged partial longitudinal cross-sectional view of a vessel, illustrating two prior art longitudinally-spaced sealed areas.

The consistent and predictable mid-seal separation created by the present invention offers substantial advantages in redundancy. It is not unusual during surgery to create multiple sealed areas 270 and 272 which are slightly longitudinally spaced from one another along the length of a vessel 274, as shown in FIG. 24. The belief is that if the primary or upstream sealed area 270 ruptures or fails, the remaining secondary backup or redundant downstream sealed area 272 will hold, thus preventing a leak. This belief is prevalent even though a significant number of instances of failure of the upstream or primary sealed area are edge-seal leaks 240 (FIG. 17) or mid-seal wall leaks 256 (FIG. 18), also shown respectively in FIGS. 25 and 26. Under circumstances of an edge-seal leak or a mid-seal wall leak, the secondary or downstream backup sealed area 272 is totally ineffective to prevent fluid loss due to the rupture through the wall of the vessel upstream of the backup sealed area.

Figure 25:
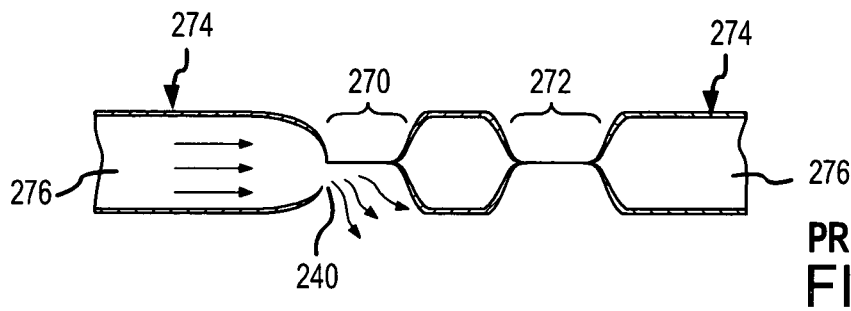
FIG. 25 is a longitudinal cross-sectional view similar to FIG. 24, illustrating a prior art edge-seal leak also shown in FIG. 17.
Figure 26:
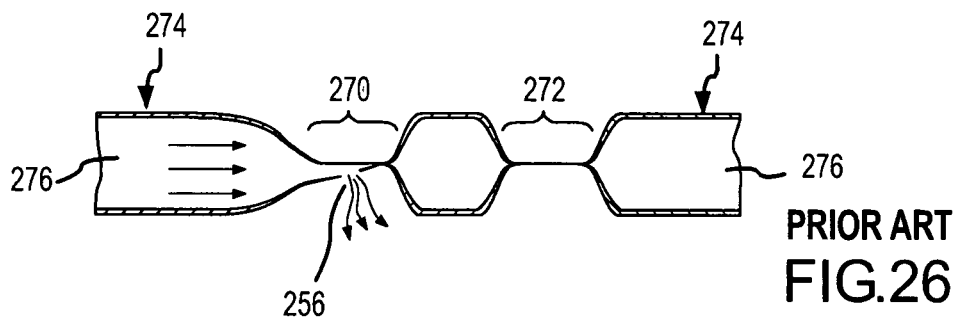
FIG. 26 is a longitudinal cross-sectional view similar to FIG. 24, illustrating a prior art mid-seal wall leak also shown in FIG. 18.

Thus, the perceived benefit of sequential primary and backup seals 270 and 272 created by prior art tissue sealing techniques is almost always illusory. When the typical edge-seal leak 240 or the typical mid-seal wall leak 256 occurs at the primary sealed area 270, as shown in FIGS. 25 and 26, respectively, the leak 240 and 256 divert the fluid from a lumen 276 of the vessel 274 to the outside of the vessel. Under such circumstances, the secondary or backup sealed area 272 has no ability to restrain the fluid within the lumen 276 because the leaks 240 and 256 have diverted the fluid away from the backup sealed area 272. The backup sealed area 272 therefore has no ability and no utility to restrain bleeding under typical prior-art sealed-area failure-mode circumstances. The significant occurrences of prior art edge-seal leaks or mid-seal wall leaks, even if as low statistically as 20%, does not provide effective redundancy or backup.

Figure 27:
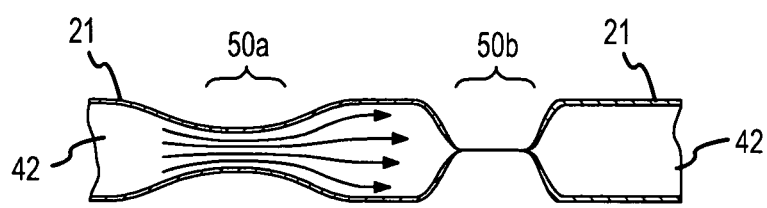
FIG. 27 is a longitudinal cross-sectional view related to FIG. 24, illustrating a mid-seal separation, also shown in FIGS. 22 and 23, of a first one of two sequential sealed areas in accordance with the present invention.

On the other hand as a result of using the present invention as shown in FIG. 27, a mid-seal separation at a primary sealed area 50a still confines the fluid within the lumen 42 of the vessel 21 and conducts that fluid within the lumen 42 to a backup sealed area 50b. The strength of the vessel walls at the previously-sealed area 50a is sufficient to confine the fluid within the lumen 42 without rupture. Consequently, the fluid pressure is applied to the backup sealed area 50b where that backup sealed area 50b has the opportunity to provide effective redundancy to prevent fluid leaks from the sealed vessel 21. Practical use of the present invention within its defined and preferred parameters has never resulted in an edge-seal leak or a mid-seal wall leak, after creating many hundreds of seals. Effective redundancy and backup is therefore achieved by the present invention.

Although the sealed areas created by the present invention normally have sufficient strength and integrity as to achieve a relatively low probability of failure, the beneficial use of multiple seals substantially diminishes the risk of internal bleeding. Moreover, the substantially diminished risk of internal bleeding is enhanced by the reliability of obtaining consistent seals of high integrity with each fusion procedure performed in accordance with the present invention.

Another benefit of the present invention relates to the common practice of forming overlapping seals. An overlapping seal is formed from a first seal on a vessel in the typical manner, coupled with forming a second seal in which the sealed area of the second seal overlaps a portion of the sealed area of the first seal. Overlapping sealing is typically applied to seal large vessels where the perception is that additional energy is required because of the size of the large vessel. The second seal may overlap the initially sealed area by approximately 50% up to 100%. To do so, the first sealed area is compressed and heated again, along with any previously unsealed adjoining tissue depending upon the degree of overlap. A 100% overlap involves performing second sealing procedure entirely coincidentally with the initial seal.

The present invention is beneficial in performing overlapped sealing because the heat created from the impulse of electrical power does not dissipate to the surrounding vessel walls to a sufficient degree to damage the vessel. Reducing or minimizing the damage of the vessel walls adjacent to the seal allows subsequent applications of energy to be effective in reinforcing previous seals, because the vessel has not been previously damaged by the excessive application of heat.

The benefits and improvements of the present invention are numerous and significant. The efficiency of vessel fusion procedures is increased by delivering the high power impulses which create the heat for fusion. Reliable vessel seals are created considerably faster than with the prior art tissue fusion techniques now commonly used. The vessel seals are significantly stronger and more reliable than the seals created using common prior art tissue fusion devices. The mid-seal separation failure mode confines the fluid within the vessel, thereby simplifying the process of re-sealing the vessel. Multiple sequential seals on a single vessel ensure that the probability of ultimate seal failure is extremely low because the mid-seal separation failure mode allows the multiple sequential seals to achieve effective redundancy, unlike known prior art tissue fusion devices. Overlapping sealing may also be beneficially applied because of the ability of the present invention to confine the energy to the sealed area without significantly spreading that energy to damage adjacent tissues and because the initial energy application has not substantially compromised the tissue strength or pliability of the sealed area. An immediate mid-seal separation allows the seal to be corrected.

The significance of these and many other improvements and advantages will become apparent upon gaining a full appreciation of the ramifications and improvements of the present invention. Preferred embodiments of the invention and many of its improvements have been described with a degree of particularity. The description is of preferred examples of implementing the invention, but the description is not necessarily intended to limit the scope of the invention. The scope of the invention is defined by the following claims.

The invention claimed:

1. Apparatus to fuse together two pieces of biological tissue at a tissue fusion interface in a tissue fusion procedure, comprising:
    a tissue fusion instrument including an upper and a lower jaw, each of the jaws comprising
        a heating element that develops a thermal energy from an electrical power impulse supplied thereto,
        a working surface which is adapted to contact a piece of tissue and transfer the thermal energy from the jaw to the contacted piece of tissue, the working surface having a longitudinal dimension, and
        a temperature sensor which supplies a sensed temperature signal related to a temperature of the working surface;
    a movement mechanism operative to move the upper jaw and the lower jaw toward one another and adapted to compress the two pieces of tissue together between the working surface of the upper jaw and the working surface of the lower jaw to a predetermined thickness in the range of 0.05 mm to 0.10 mm to fuse the two pieces of tissue together at the tissue fusion interface from a combination of the compression and the thermal energy, wherein the movement mechanism is adapted to move the working surface of the upper jaw and the working surface of the lower jaw toward one another with the longitudinal dimension of the working surface of the upper jaw parallel to the longitudinal dimension of the working surface of the lower jaw during compression of the two pieces of tissue to the predetermined thickness, and wherein the movement mechanism is operative to transfer a force from the working surfaces during compression of the two pieces of tissue, the force being measurable to create a force signal that is compared to determine when the two pieces of tissue have been compressed; and a power control device connected to the tissue fusion instrument, the power control device being responsive to the force signal and to each of the sensed temperature signals to separately regulate a duration and an amount of electrical energy provided in each of the electrical power impulse supplied to the upper jaw and the electrical power impulse supplied to the lower jaw, the power control device limiting the duration of each of the electrical power impulses to a predetermined time duration of no greater than 4.0 seconds, the power control device controlling the amount of electrical energy provided in each of the electrical power impulses to attain and maintain a predetermined temperature in the range of 150° C. to 200° C. at each of the upper jaw and the lower jaw during the respective predetermined time duration.

2. Apparatus as defined in claim 1, wherein said predetermined time duration is no greater than 2.0 seconds.

3. Apparatus as defined in claim 2, wherein the two pieces of tissue are apposite walls of a blood vessel.

4. Apparatus as defined in claim 3, wherein:
each of the electrical power impulses produces an energy density at each of the working surfaces of at least 155 W/cm² of an effective area of the respective working surface;
each of the jaws and their respective working surfaces are formed of ceramic material having a thermal conductivity of at least 140 W/m° K; each of the working surfaces has a smoothness defined by an Ra of 0.40 microns or less; and
the movement mechanism produces a pressure on the two pieces of tissue at the tissue fusion interface in the range of 0.88 N/mm² to 1.2 N/mm² of the effective area of the respective working surface.

5. Apparatus as defined in claim 1, wherein said predetermined time duration is approximately 0.5 seconds.

6. Apparatus as defined in claim 5, wherein the two pieces of tissue are apposite walls of a blood vessel.

7. Apparatus as defined in claim 6, wherein:
the amount of electrical energy provided in each of the electrical power impulses supplied to each of the heating elements produces an energy density at the respective working surface of at least 155 W/cm2 of an effective area of the respective working surface;
each of the jaws and their respective working surfaces are formed of ceramic material having a thermal conductivity of at least 140 W/m° K;
each of the working surfaces each have a smoothness defined by an Ra of 0.40 microns or less; and
the movement mechanism produces a pressure on the two pieces of tissue at the tissue fusion interface in the range of 0.88 N/mm2 to 1.2 N/mm² of the effective area of the respective working surface.

8. Apparatus as defined in claim 1, wherein said predetermined time duration is in a range of 0.5 seconds to 2.0 seconds.

9. Apparatus as defined in claim 8, wherein the pieces of tissue are apposite walls of a blood vessel.

10. Apparatus as defined in claim 9, wherein:
the amount of electrical energy provided in each of the electrical power impulses supplied to each of the heating elements produces an energy density at the respective working surface of at least 155 W/cm2 of an effective area of the respective working;
each of the jaws and the working surfaces are formed of ceramic material having a thermal conductivity of at least 140 W/m° K;
each of the working surfaces each have a smoothness defined by an Ra of 0.40 microns or less; and
the movement mechanism produces a pressure on the two pieces of tissue at the tissue fusion interface in the range of 0.88 N/mm² to 1.2 N/mm² of the effective area of the respective working surface.

11. Apparatus as defined in claim 1, wherein the amount of electrical energy provided in each of the electrical power impulses elevates the temperature of the respective working surface at a rate in the range of between 150° C. per second to 500° C. or greater per second.

12. Apparatus as defined in claim 1, wherein the amount of electrical energy provided in each of the electrical power impulses produces an energy density at the respective working surface of at least 155 W/cm² of an effective area of the respective working surface.

13. Apparatus as defined in claim 12, wherein the two pieces of tissue are apposite walls of a blood vessel.

14. Apparatus as defined in claim 1, wherein the amount of electrical energy provided in each of the electrical power impulses produces an energy density at the respective working surface of at least 233 W/cm² of an effective area of the respective working surface.

15. Apparatus as defined in claim 14, wherein the two pieces of tissue are apposite walls of a blood vessel.

16. Apparatus as defined in claim 1, wherein the movement mechanism includes a lock to operatively hold the upper jaw and the lower jaw in a held position where the two pieces of tissue are compressed between the working surface of the upper jaw and the working surface of the lower jaw to the predetermined thickness, and the movement mechanism further includes a release to operatively release the upper jaw and the lower jaw from the held position, thus releasing each of the respective working surfaces from the two pieces of tissue.

17. Apparatus as defined in claim 1, wherein the upper jaw and the lower jaw and their respective working surfaces are formed of ceramic material having a thermal conductivity of at least 140 W/m° K.

18. Apparatus as defined in claim 17, wherein each of the ceramic working surfaces has a smoothness defined by an Ra of 0.40 microns or less.

19. Apparatus as defined in claim 17, wherein each of the ceramic working surfaces has a smoothness defined by an Ra of no greater than 0.25 microns.

20. Apparatus as defined in claim 17, wherein each of the ceramic working surfaces has a smoothness defined by an Ra of approximately 0.15 microns or less.

21. Apparatus as defined in claim 1, wherein each of the electrical power impulses is formed by direct current conducted to the respective heating element by the power control device.

22. Apparatus as defined in claim 1, wherein each of the working surfaces has a smoothness defined by an Ra of no greater than 0.25 microns.

23. Apparatus as defined in claim 1, wherein each of the working surfaces has a smoothness defined by an Ra of approximately 0.15 microns or less.

24. Apparatus as defined in claim 1, wherein the compression of the two pieces of tissue at the tissue fusion interface is in the range of 0.88 N/mm² to 1.2 N/mm² of an effective area of the respective working surface.

25. Apparatus as defined in claim 24, wherein the two pieces of tissue are apposite walls of a blood vessel.

26. Apparatus as defined in claim 1, wherein a fusion strength between the two pieces of tissue at the tissue fusion interface after fusion is less than the inherent strength of each of the two pieces of tissue adjoining the fused tissue fusion interface to allow separation of the two pieces of tissue at the tissue fusion interface before breaching either of the tissue pieces adjoining the two pieces of tissue at tissue fusion interface.

27. Apparatus as defined in claim 1, wherein the two pieces of tissue are apposite walls of a blood vessel.

28. Apparatus as defined in claim 1, wherein the working surface of one of the upper jaw and the lower jaw curves convexly toward the working surface of the other one of the upper jaw and the lower jaw in a direction transverse to the respective longitudinal dimension.

29. Apparatus as defined in claim 1, wherein the power control device separately regulates the duration and the amount of electrical energy provided in each of the electrical power impulses on a basis of a proportional, integral and derivative algorithm.

30. Apparatus as defined in claim 1, wherein each of the working surfaces has a smoothness defined by an Ra of 0.40 microns or less.

31. Apparatus as defined in claim 1, wherein: the force signal is supplied by a sensor mounted on a handle.

32. Apparatus as defined in claim 1, wherein:
the power control device responds to the force signal to initiate delivery of each of the electrical power impulses when the force signal indicates compression of the two pieces of tissue to the predetermined thickness at the tissue fusion interface.

\* \* \* \* \*